United States Patent
Raghavan et al.

(10) Patent No.: US 12,364,481 B2
(45) Date of Patent: Jul. 22, 2025

(54) INTELLIGENT ANVIL FOR CIRCULAR SURGICAL STAPLER

(71) Applicant: Cilag GmbH International, Zug (CH)

(72) Inventors: Devanathan Raghavan, Mason, OH (US); John K. Bruce, Morrow, OH (US); Chad P. Boudreaux, Cincinnati, OH (US)

(73) Assignee: CILAG GMBH INTERNATIONAL, Zug (CH)

(*) Notice: Subject to any disclaimer, the term of this patent is extended or adjusted under 35 U.S.C. 154(b) by 0 days.

(21) Appl. No.: 18/500,525

(22) Filed: Nov. 2, 2023

(65) Prior Publication Data

US 2025/0143706 A1    May 8, 2025

(51) Int. Cl.
*A61B 17/115* (2006.01)
*A61B 90/00* (2016.01)

(52) U.S. Cl.
CPC .......... *A61B 17/1155* (2013.01); *A61B 90/08* (2016.02); *A61B 2090/0811* (2016.02)

(58) Field of Classification Search
CPC . A61B 17/07207; A61B 90/06; A61B 17/115; A61B 17/0686; A61B 34/10; A61B 17/128; A61B 17/068; A61B 17/1155; A61B 17/072; A61B 2017/07214; A61B 2090/065; A61B 2090/061; A61B 2090/0811; A61B 2017/00106; A61B 17/29; A61B 2017/00039; A61B 2017/00022; A61B 2017/00119

See application file for complete search history.

(56) References Cited

U.S. PATENT DOCUMENTS

| | | | |
|---|---|---|---|
| 5,205,459 A | 4/1993 | Brinkerhoff et al. | |
| 5,271,544 A | 12/1993 | Fox et al. | |
| 5,275,322 A | 1/1994 | Brinkerhoff et al. | |
| 5,285,945 A | 2/1994 | Brinkerhoff et al. | |
| 5,292,053 A | 3/1994 | Bilotti et al. | |
| 5,333,773 A | 8/1994 | Main et al. | |
| 5,350,104 A | 9/1994 | Main et al. | |
| 5,533,661 A | 7/1996 | Main et al. | |
| 7,717,312 B2 * | 5/2010 | Beetel | A61B 17/0686 227/176.1 |
| 8,002,795 B2 * | 8/2011 | Beetel | A61B 17/07207 227/176.1 |
| 8,579,177 B2 * | 11/2013 | Beetel | A61B 17/068 227/176.1 |

(Continued)

*Primary Examiner* — Nathaniel C Chukwurah
(74) *Attorney, Agent, or Firm* — FROST BROWN TODD LLP

(57) ABSTRACT

A surgical instrument includes a body assembly, a shaft assembly, a stapling head assembly disposed at a distal end of the shaft assembly, and an anvil. The stapling head assembly having a deck member and a closure shaft capable of moving relative to the deck member. The anvil including a head, a shank, a biasing body, and a electronic unit having a distance sensor. The head and the shank being capable of moving relative to each other. The biasing body being interposed between the head and the shank with a known spring constant. The distance sensor being capable of measuring a relative distance between the shank and the head, while the electronic unit can communicate a parameter associated with the relative distance to a console.

18 Claims, 27 Drawing Sheets

(56) References Cited

U.S. PATENT DOCUMENTS

| | | | |
|---|---|---|---|
| 8,800,839 B2* | 8/2014 | Beetel | A61B 17/115 |
| | | | 606/139 |
| 8,910,847 B2 | 12/2014 | Nalagatla et al. | |
| 9,597,081 B2* | 3/2017 | Swayze | A61B 17/1155 |
| 9,668,735 B2* | 6/2017 | Beetel | A61B 17/128 |
| 9,713,469 B2 | 7/2017 | Leimbach et al. | |
| 9,907,552 B2 | 3/2018 | Measamer et al. | |
| 9,936,949 B2 | 4/2018 | Measamer et al. | |
| 10,307,157 B2 | 6/2019 | Miller et al. | |
| 2006/0273135 A1* | 12/2006 | Beetel | A61B 17/128 |
| | | | 227/175.1 |
| 2015/0083772 A1 | 3/2015 | Miller et al. | |
| 2016/0374672 A1* | 12/2016 | Bear | H02J 7/00 |
| | | | 606/219 |
| 2017/0258471 A1* | 9/2017 | DiNardo | A61B 17/068 |

* cited by examiner

INTELLIGENT ANVIL FOR CIRCULAR SURGICAL STAPLER

BACKGROUND

In some surgical procedures (e.g., colorectal, bariatric, thoracic, etc.), portions of a patient's digestive tract (e.g., the gastrointestinal tract and/or esophagus, etc.) may be cut and removed to eliminate undesirable tissue or for other reasons. Once the tissue is removed, the remaining portions of the digestive tract may be coupled together in an end-to-end anastomosis, an end-to-side anastomosis, or a side-to-side anastomosis. The anastomosis may provide a substantially unobstructed flow path from one portion of the digestive tract to the other portion of the digestive tract, without also providing any kind of leaking at the site of the anastomosis.

One example of an instrument that may be used to provide an anastomosis is a circular stapler. Some such staplers are operable to clamp down on layers of tissue, cut through the clamped layers of tissue, and drive staples through the clamped layers of tissue to substantially seal the layers of tissue together near the severed ends of the tissue layers, thereby joining the two severed ends of the anatomical lumen together. The circular stapler may be configured to sever the tissue and seal the tissue substantially simultaneously. For instance, the circular stapler may sever excess tissue that is interior to an annular array of staples at an anastomosis, to provide a substantially smooth transition between the anatomical lumen sections that are joined at the anastomosis. Circular staplers may be used in open procedures or in endoscopic procedures. In some instances, a portion of the circular stapler is inserted through a patient's naturally occurring orifice.

Examples of circular staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910, 847, entitled "Low Cost Anvil Assembly for a Circular Stapler," issued Dec. 16, 2014. The disclosure of each of the above-cited U.S. Patents is incorporated by reference herein.

Some circular staplers may include a motorized actuation mechanism. Examples of circular staplers with motorized actuation mechanisms are described in U.S. Pub. No. 2015/0083772, entitled "Surgical Stapler with Rotary Cam Drive and Return," published Mar. 26, 2015, now abandoned; U.S. Pat. No. 9,936,949, entitled "Surgical Stapling Instrument with Drive Assembly Having Toggle Features," issued Apr. 10, 2018; U.S. Pat. No. 9,907,552, entitled "Control Features for Motorized Surgical Stapling Instrument," issued Mar. 6, 2018; U.S. Pat. No. 9,713,469, entitled "Surgical Stapler with Rotary Cam Drive," issued Jul. 25, 2017; and U.S. Pub. No. 2017/0258471, entitled "Methods and Systems for Performing Circular Stapling," published Sep. 14, 2017, issued as U.S. Pat. No. 10,709,452 on Jul. 14, 2020. The disclosure of each of the above-cited U.S. Patent Publications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
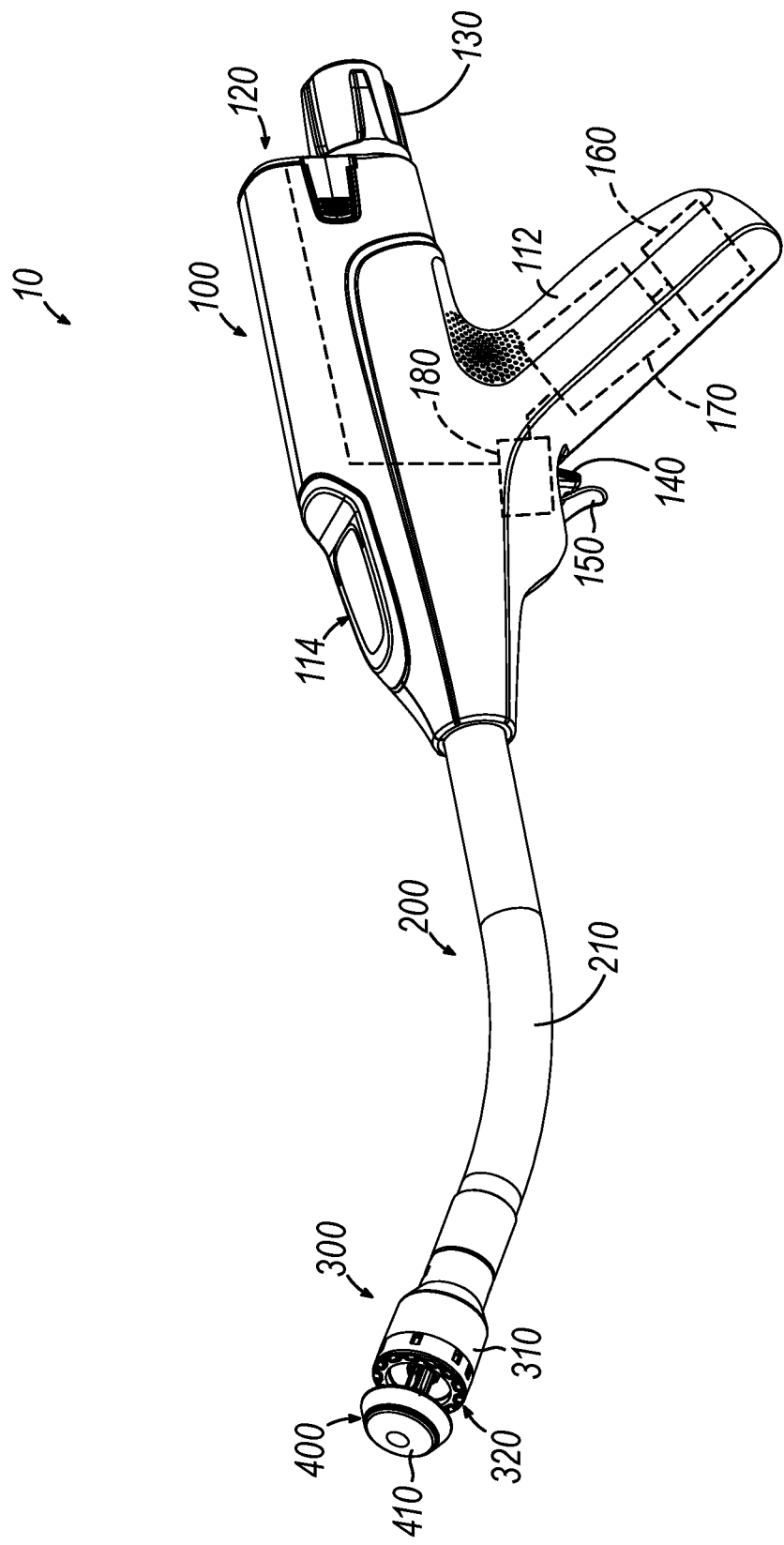
FIG. 1 depicts a perspective view of an illustrative circular surgical stapler.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "top," "bottom," "upper," "lower," "vertical," "horizontal," or the like are used herein with reference to the drawings, it will be appreciated that such terms are used for illustrative description purposes only and are not intended to be limiting or absolute. In that regard, it will be understood that surgical instruments such as those disclosed herein may be used in a variety of orientations and positions not limited to those shown and described herein.

I. Overview of Illustrative Circular Surgical Stapling Instrument

Figure 2:
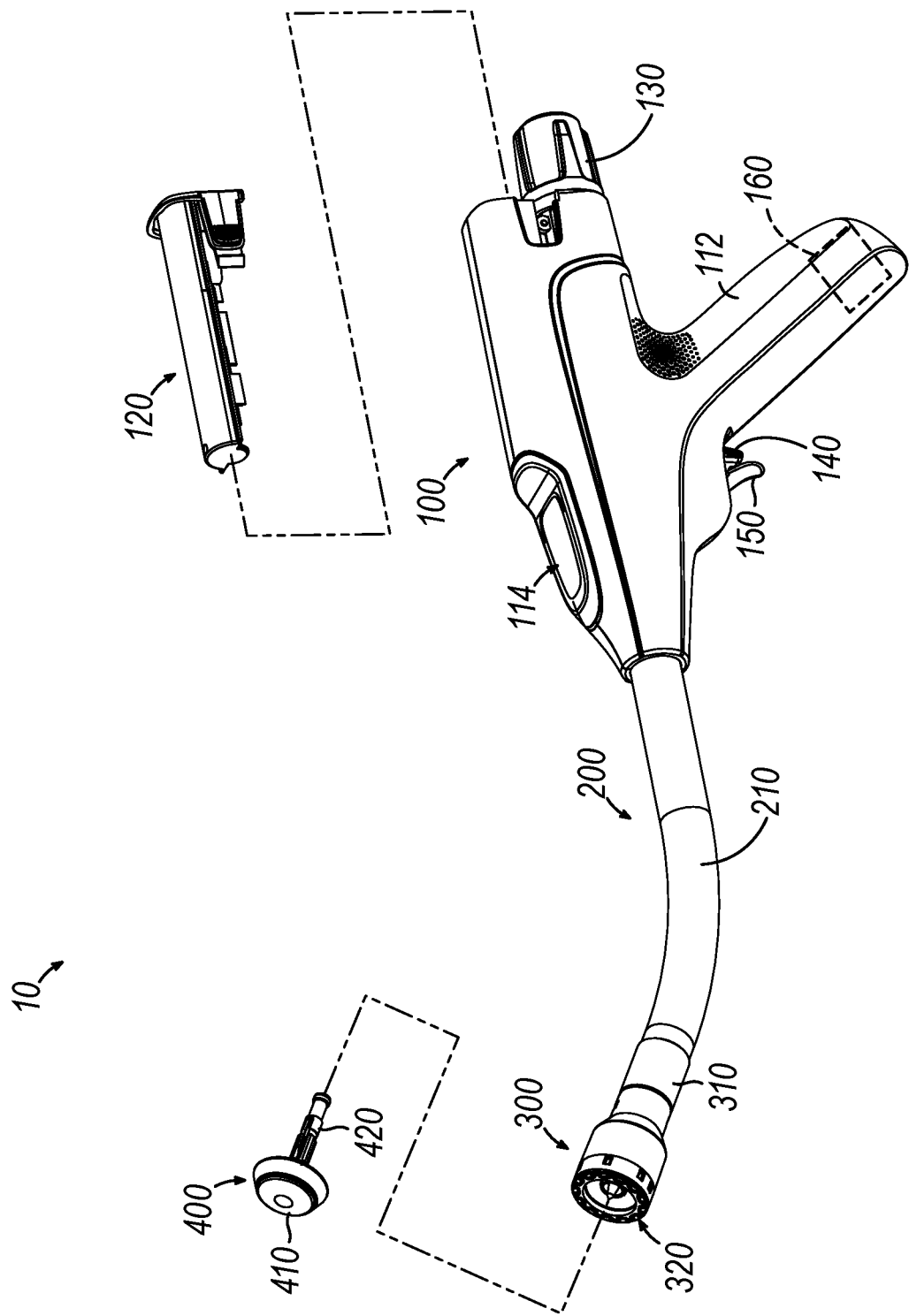
FIG. 2 depicts a perspective view of the circular stapler of FIG. 1, with a battery pack removed from a handle assembly and an anvil removed from a stapling head assembly.

FIGS. 1-2 depict an illustrative circular surgical stapling instrument (10) that may be used to provide an end-to-end, side-to-side, or end-to-side anastomosis between two sections of an anatomical lumen such as a portion of a patient's digestive tract. Instrument (10) of this example includes a body assembly (e.g. a handle assembly (100)), a shaft assembly (200) extending distally from handle assembly (100), a stapling head assembly (300) at a distal end of shaft assembly (200), and an anvil (400) configured to releasably couple and cooperate with stapling head assembly (300) to clamp, staple, and cut tissue. Instrument (10) further includes a removable battery pack (120) operable to provide electrical power to a motor (160) housed within handle assembly (100), as will be described in greater detail below, and a control module (170) housed within handle assembly (100) and configured to control motor (160) based on user input.

Shaft assembly (200) extends distally from handle assembly (100) and includes a preformed bend. In some versions, the preformed bend is configured to facilitate positioning of stapling head assembly (300) within a patient's colon. Various suitable bend angles or radii that may be used will be apparent to those skilled in the art in view of the teachings herein. In some other versions, shaft assembly (200) is straight, such that shaft assembly (200) lacks a preformed bend. Various illustrative components that may be incorporated into shaft assembly (200) will be described in greater detail below.

Stapling head assembly (300) is located at the distal end of shaft assembly (200). As shown in FIGS. 1-2 and as will be described in greater detail below, anvil (400) is configured to removably couple with shaft assembly (200), adjacent to stapling head assembly (300). As will also be described in greater detail below, anvil (400) and stapling head assembly (300) are configured to cooperate to manipulate tissue in three ways, including clamping the tissue, cutting the tissue, and stapling the tissue. A knob (130) at the proximal end of handle assembly (100) is rotatable relative to casing (110) to provide precise clamping of the tissue between anvil (400) and stapling head assembly (300). When a safety trigger (140) of handle assembly (100) is pivoted away from a firing trigger (150) of handle assembly (100), firing trigger (150) may be actuated to thereby provide cutting and stapling of the tissue.

A. Illustrative Anvil

Figure 3:
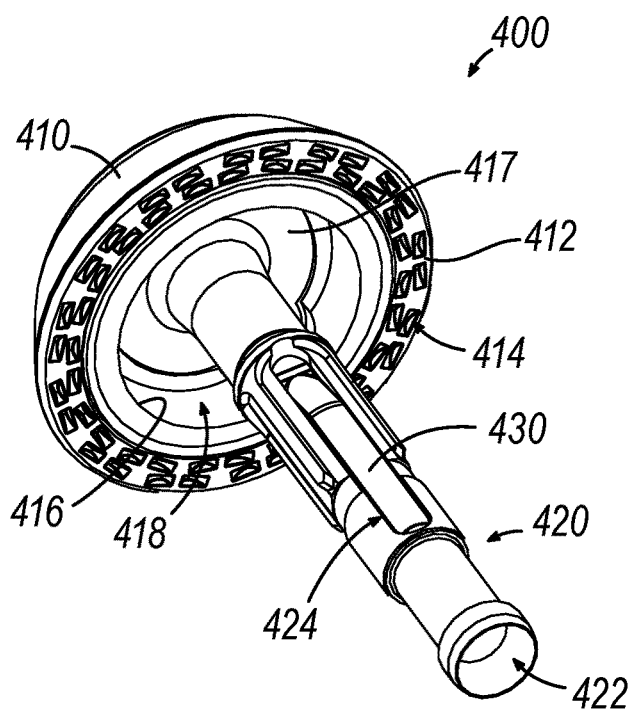
FIG. 3 depicts a perspective view of the anvil of the circular stapler of FIG. 1.

As best seen in FIG. 3, anvil (400) of the present example comprises a head (410) and a shank (420). Head (410) includes a proximal surface (412) that defines a plurality of staple forming pockets (414). Staple forming pockets (414) are arranged in two concentric annular arrays in the present example. In some other versions, staple forming pockets (414) are arranged in three or more concentric annular arrays. Staple forming pockets (414) are configured to deform staples as the staples are driven into staple forming pockets (414). For instance, each staple forming pocket (414) may deform a generally "U" shaped staple into a "B" shape as is known in the art. Proximal surface (412) terminates at an inner edge (416), which defines an outer boundary of an annular recess (418) surrounding shank (420).

Shank (420) defines a bore (422) and includes a pair of pivoting latch members (430). Latch members (430) are positioned within bore (422) such that the distal ends are positioned at the proximal ends of lateral openings (424), which are formed through the sidewall of shank (420). Lateral openings (424) thus provide clearance for the distal ends and latch shelves (436) to deflect radially outwardly from the longitudinal axis defined by shank (420). However, latch members (430) are configured to resiliently bias the distal ends and latch shelves (436) to pivot radially inwardly toward the longitudinal axis defined by shank (420). Latch members (430) thus act as retaining clips. This allows anvil (400) to be removably secured to an actuatable closure member (also referred to a closure shaft) in the form of a trocar (330) of stapling head assembly (300), as will be described in greater detail below. It should be understood, however, that latch members (436) are merely optional. Anvil (400) may be removably secured to trocar (330) using any other suitable components, features, or techniques.

B. Illustrative Stapling Head Assembly

Figure 4:
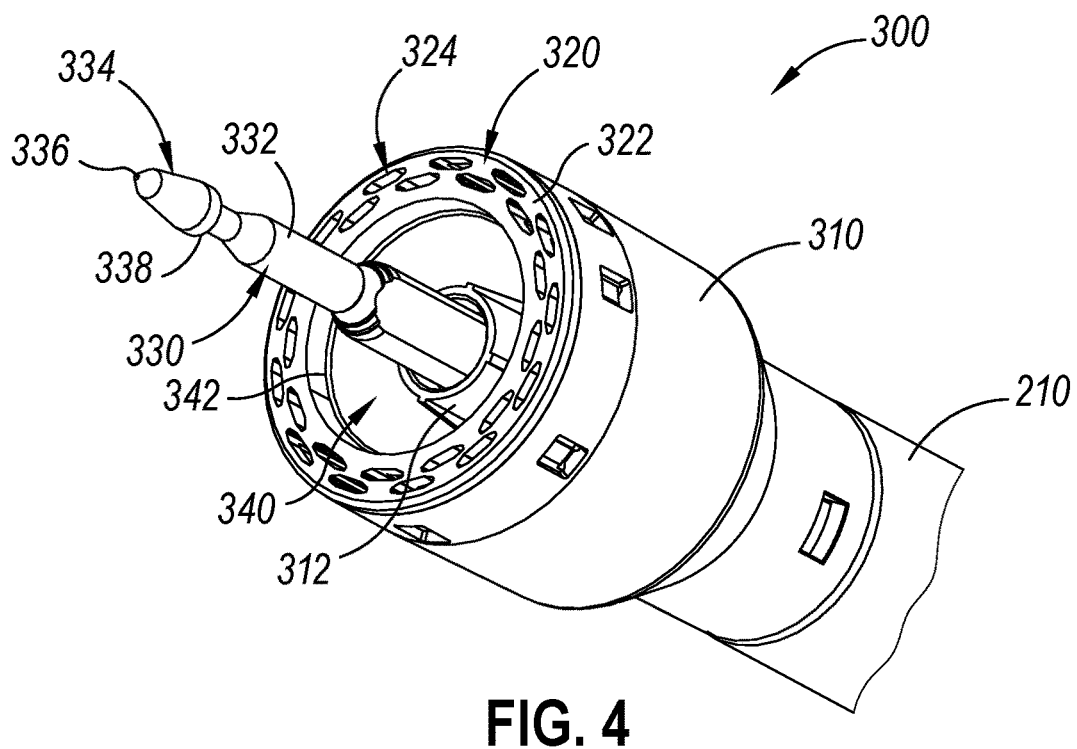
FIG. 4 depicts a perspective view of the stapling head assembly of the circular stapler of FIG. 1.
Figure 5:
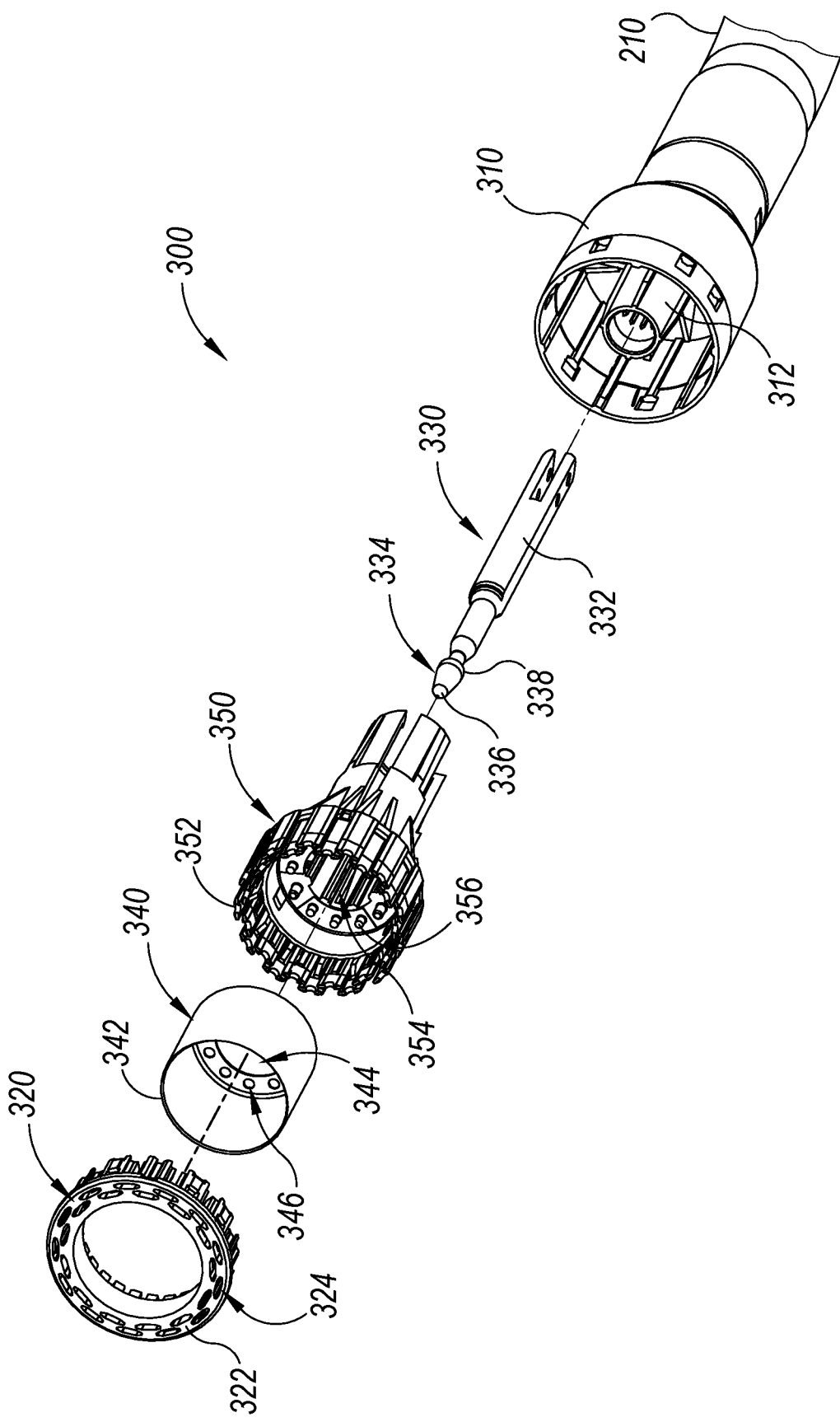
FIG. 5 depicts an exploded perspective view of the stapling head assembly of FIG. 4.

As best seen in FIGS. 4 and 5, stapling head assembly (300) of the present example is coupled to a distal end of shaft assembly (200) and comprises a body member (310) and a staple driver member (350) slidably housed therein. Body member (310) includes a distally extending cylindraceous inner core member (312). Body member (310) is fixedly secured to an outer sheath (210) of shaft assembly (200), and body member (310) and outer sheath (210) thus serve together as a mechanical ground for stapling head assembly (300). In some versions, stapling head assembly (300) may be configured to releasably couple with the distal end of shaft assembly (200), for example as disclosed in U.S. Pat. No. 9,597,081, entitled "Motor Driven Rotary Input Circular Stapler with Modular End Effector," issued Mar. 21, 2017, the disclosure of which is incorporated by reference herein.

Trocar (330) is positioned coaxially within inner core member (312) of body member (310). As will be described in greater detail below, trocar (330) is operable to translate distally and proximally relative to body member (310) in response to rotation of knob (130) relative to casing (110) of handle assembly (100). Trocar (330) comprises a shaft (332) and a head (334). Head (334) includes a pointed tip (336) and an inwardly extending proximal surface (338). Shaft (332) thus provides a reduced outer diameter just proximal to head (334), with surface (338) providing a transition between that reduced outer diameter of shaft (332) and the outer diameter of head (334). While tip (336) is pointed in the present example, tip (336) is not sharp. Tip (336) will thus not easily cause trauma to tissue due to inadvertent contact with tissue. Head (334) and the distal portion of shaft (332) are configured for insertion in bore (422) of anvil (400). Proximal surface (338) and latch shelves (436) have complementary positions and configurations such that latch shelves (436) engage proximal surface (338) when shank (420) of anvil (400) is fully seated on trocar (330). Anvil (400) is thus secured to trocar (330) through a snap fit provided by latch members (430).

Staple driver member (350) is operable to actuate longitudinally within body member (310) in response to activation of motor (160) as will be described in greater detail below. Staple driver member (350) of the present example includes two distally presented concentric annular arrays of staple drivers (352). Staple drivers (352) are arranged to correspond with the arrangement of staple forming pockets (414) of anvil (400). Thus, each staple driver (352) is configured to drive a corresponding staple into a corresponding staple forming pocket (414) when stapling head assembly (300) is actuated. It should be understood that the arrangements of staple drivers (352) and staple forming pockets (414) shown herein may be modified in any suitable manner, provided that staple drivers (352) and staple forming pockets (414) are configured to align with one another to provide proper formation of staples. Staple driver member (350) also defines a bore (354) that is configured to coaxially receive core member (312) of body member (310). An annular array of studs (356) project distally from a distally presented surface surrounding bore (354).

A cylindraceous knife member (340) is coaxially positioned within staple driver member (350). Knife member (340) includes a distally presented, sharp circular cutting edge (342). Knife member (340) is sized such that knife member (340) defines an outer diameter that is smaller than the diameter defined by the inner annular array of staple drivers (352). Knife member (340) also defines an opening that is configured to coaxially receive core member (312) of body member (310). An annular array of openings (346) formed in knife member (340) is configured to complement the annular array of studs (356) of staple driver member (350), such that knife member (340) is fixedly secured to staple driver member (350) via studs (356) and openings (346). By way of example only, studs (356) may be heat staked to knife member (340) using techniques known in the art. Other suitable structural relationships between knife member (340) and stapler driver member (350) will be apparent to those skilled in the art in view of the teachings herein.

A deck member (320) is fixedly secured to a distal end of body member (310). Deck member (320) includes a distally presented deck surface (322) defining two concentric annular arrays of staple openings (324). Staple openings (324) are arranged to correspond with the arrangement of staple drivers (352) and staple forming pockets (414) described above. Thus, each staple opening (324) is configured to provide a path for a corresponding staple driver (352) to drive a corresponding staple through deck member (320) and into a corresponding staple forming pocket (414) when stapling head assembly (300) is actuated. It should be understood that the arrangement of staple openings (324) may be modified to correspond with the arrangement of drivers (352) and staple forming pockets (414) described above. It should also be understood that various structures and techniques may be used to contain staples within stapling head assembly (300) before stapling head assembly (300) is actuated. Such structures and techniques that are used to contain staples within stapling head assembly (300) may prevent the staples from inadvertently falling out through staple openings (324) before stapling head assembly (300) is actuated. Various suitable forms that such structures and techniques may take will be apparent to those skilled in the art in view of the teachings herein.

Referring to FIG. 5, deck member (320) defines an inner diameter that is just slightly larger than the outer diameter defined by knife member (340). Deck member (320) is thus configured to allow knife member (340) to translate distally to a point where cutting edge (342) is distal to deck surface (322).

In some versions of instrument (10) it may be desirable to provide instrument (10) with features that are configured to indicate proper and/or improper attachment of anvil (400) to trocar (330) of stapling head assembly (300). For instance, if anvil (400) is not properly attached to trocar (330), an operator may receive audible and/or tactile feedback indicating improper attachment. Additionally, if anvil (400) is properly attached to trocar (330), an operator may receive audible, tactile, and/or visible feedback indicating proper attachment. In addition, or in the alternative, features may be configured to prevent firing of stapling head assembly (300) unless anvil (400) is properly attached to trocar (330). For instance, if anvil (400) is not properly attached to trocar (330), stapling head assembly (300) may be prevented from firing. If anvil (400) is properly attached to trocar (330), firing of stapling head assembly (300) may be enabled. Such features may include various types of visual indicia, sensors, switches, and the like. By way of example only, such features may include those of the type disclosed in U.S. Pat. No. 10,307,157, entitled "Surgical Stapler with Anvil Seating Detection," issued Jun. 4, 2019, and U.S. Pub. No. 2017/0258471, entitled "Methods and Systems for Performing Circular Stapling," published Sep. 14, 2017, issued as U.S. Pat. No. 10,709,452 on Jul. 14, 2020, the disclosures of which are incorporated by reference herein.

C. Illustrative Shaft Assembly

Figure 6:
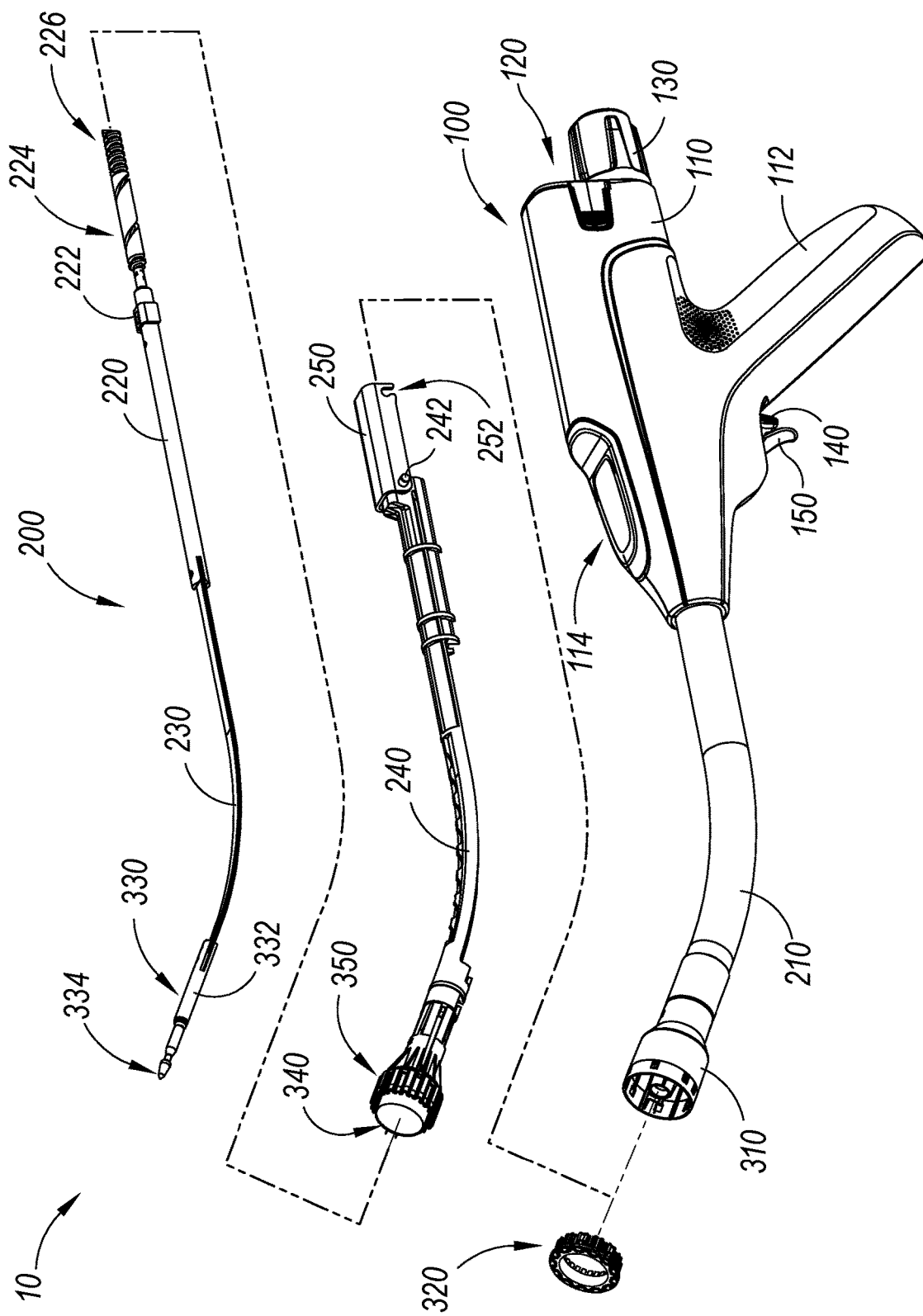
FIG. 6 depicts an exploded perspective view of the circular stapler of FIG. 1, with portions of the shaft assembly shown separated from each other.

FIG. 6 shows various components of shaft assembly (200), which couples components of stapling head assembly (300) with components of handle assembly (100). In particular, and as noted above, shaft assembly (200) includes an outer sheath (210) that extends between handle assembly (100) and body member (310). In the present example, outer sheath (210) is rigid and includes a preformed curved section as noted above.

Shaft assembly (200) further includes a trocar actuation rod (220) and a trocar actuation band assembly (230). The distal end of trocar actuation band assembly (230) is fixedly secured to the proximal end of trocar shaft (332). The proximal end of trocar actuation band assembly (230) is fixedly secured to the distal end of trocar actuation rod (220). It should therefore be understood that trocar (330) will translate longitudinally relative to outer sheath (210) in response to translation of trocar actuation band assembly (230) and trocar actuation rod (220) relative to outer sheath (210). Trocar actuation band assembly (230) is configured to flex such that trocar actuation band assembly (230) may follow along the preformed curve in shaft assembly (200) as trocar actuation band assembly (230) is translated longitudinally relative to outer sheath (210). However, trocar actuation band assembly (230) has sufficient column strength and tensile strength to transfer distal and proximal forces from trocar actuation rod (220) to trocar shaft (332). Trocar actuation rod (220) is rigid. A clip (222) is fixedly secured to trocar actuation rod (220) and is configured to cooperate with complementary features within handle assembly (100) to prevent trocar actuation rod (220) from rotating within handle assembly (100) while still permitting trocar actuation rod (220) to translate longitudinally within handle assembly (100). Trocar actuation rod (220) further includes a coarse helical threading (224) and a fine helical threading (226).

Shaft assembly (200) further includes a stapling head assembly driver (240) that is slidably received within outer sheath (210). The distal end of stapling head assembly driver (240) is fixedly secured to the proximal end of staple driver member (350). The proximal end of stapling head assembly driver (240) is secured to a drive bracket (250) via a pin (242). It should therefore be understood that staple driver member (350) will translate longitudinally relative to outer sheath (210) in response to translation of stapling head assembly driver (240) and drive bracket (250) relative to outer sheath (210). Stapling head assembly driver (240) is configured to flex such that stapling head assembly driver (240) may follow along the preformed curve in shaft assembly (200) as stapling head assembly driver (240) is translated longitudinally relative to outer sheath (210). However, stapling head assembly driver (240) has sufficient column strength to transfer distal forces from drive bracket (250) to staple driver member (350).

D. Illustrative Handle Assembly and User Input Features

As shown in FIG. 1, handle assembly (100) includes a casing (110) having a lower portion that defines an obliquely oriented pistol grip (112) and an upper portion that supports a user interface feature (114) and receives a battery pack (120), as described in greater detail below. Handle assembly (100) further includes several features that are operable to actuate anvil (400) and stapling head assembly (300). In particular, handle assembly (100) includes a rotatable knob (130), a safety trigger (140) a firing trigger (150), a motor (160), and a motor activation module (180). Knob (130) is coupled with trocar actuation rod (220) via a nut (not shown), such that coarse helical threading (224) will selectively engage a thread engagement feature within the interior of the nut; and such that fine helical threading (226) will selectively engage a thread engagement feature within the interior of knob (130). These complementary structures are configured such that trocar actuation rod (220) will first translate proximally at a relatively slow rate, then translate proximally at a relatively fast rate, in response to rotation of knob (130).

It should be understood that when anvil (400) is coupled with trocar (330), rotation of knob (130) will provide corresponding translation of anvil (400) relative to stapling head assembly (300). It should also be understood that knob (130) may be rotated in a first angular direction (e.g., clockwise) to retract anvil (400) toward stapling head assembly (300); and in a second angular direction (e.g., counterclockwise) to advance anvil (400) away from stapling head assembly (300). Knob (130) may thus be used to adjust a gap distance (d) between opposing surfaces (412, 322) of anvil (400) and stapling head assembly (300) until a suitable gap distance (d) has been achieved, for example as shown in FIG. 7C described below.

Firing trigger (150) is operable to activate motor (160) to thereby actuate stapling head assembly (300). Safety trigger (140) is operable to selectively block actuation of firing trigger (150) based on the longitudinal position of anvil (400) in relation to stapling head assembly (300). Handle assembly (100) also includes components that are operable to selectively lock out both triggers (140, 150) based on the position of anvil (400) relative to stapling head assembly (300). For instance, safety trigger (140) may be blocked from rotating from an engaged position to a disengaged position until the position of anvil (400) relative to stapling head assembly (300) is within a predefined range. Accordingly, until the anvil position is within the predefined range, actuation of firing trigger (150) is blocked by safety trigger (140), thereby inhibiting firing of stapling head assembly (300).

Firing trigger (150) of the present example includes an integral actuation paddle (not shown), which may be similar to the paddle disclosed in U.S. Pub. No. 2017/0258471, issued as U.S. Pat. No. 10,709,452 on Jul. 14, 2020, incorporated by reference above. The paddle is configured to actuate a switch of motor activation module (180) (FIG. 1) when firing trigger (150) is pivoted to a fired position. Motor activation module (180) is in communication with battery pack (120) and motor (160), such that motor activation module (180) is configured to provide activation of motor (160) with electrical power from battery pack (120) in response to the paddle actuating the switch of motor activation module (180). Thus, motor (160) will be activated when firing trigger (150) is pivoted. This activation of motor (160) will actuate stapling head assembly (300) via drive bracket (250), as described in greater detail below. Though not shown, and by way of example only, motor (160) may be operatively coupled with drive bracket (250) via a gearbox coupled with an output shaft of motor (160), a rotary cam member coupled with an output shaft of the gearbox, and a cam follower coupled with the rotary cam member, for example as disclosed in U.S. Pub. No. 2017/0258471, issued as U.S. Pat. No. 10,709,452 on Jul. 14, 2020, incorporated by reference above.

As best shown in FIGS. 1-2, handle assembly (100) is further configured to releasably receive a battery pack (120) operable to provide electrical power to motor (160), as noted above. It should be understood that battery pack (120) and handle assembly (100) may have complementary electrical contacts, pins and sockets, and/or other features that provide paths for electrical communication from battery pack (120) to electrically powered components in handle assembly (100) when battery pack (120) is coupled with handle assembly (100). It should also be understood that, in some versions, battery pack (120) may be unitarily integrated within handle assembly (100) such that battery back (120) cannot be removed from handle assembly (100).

E. Illustrative Anastomosis Procedure with Circular Stapling Instrument

FIGS. 7A-7E show instrument (10) being used to form an anastomosis (70) between two tubular anatomical structures (20, 40). By way of example only, the tubular anatomical structures (20, 40) may comprise sections of a patient's esophagus, sections of a patient's colon, other sections of the patient's digestive tract, or any other tubular anatomical structures. In some versions, one or more diseased portions of a patient's colon are removed, with the tubular anatomical structures (20, 40) of FIGS. 7A-7E representing the remaining severed portions of the colon.

Figure 7A:
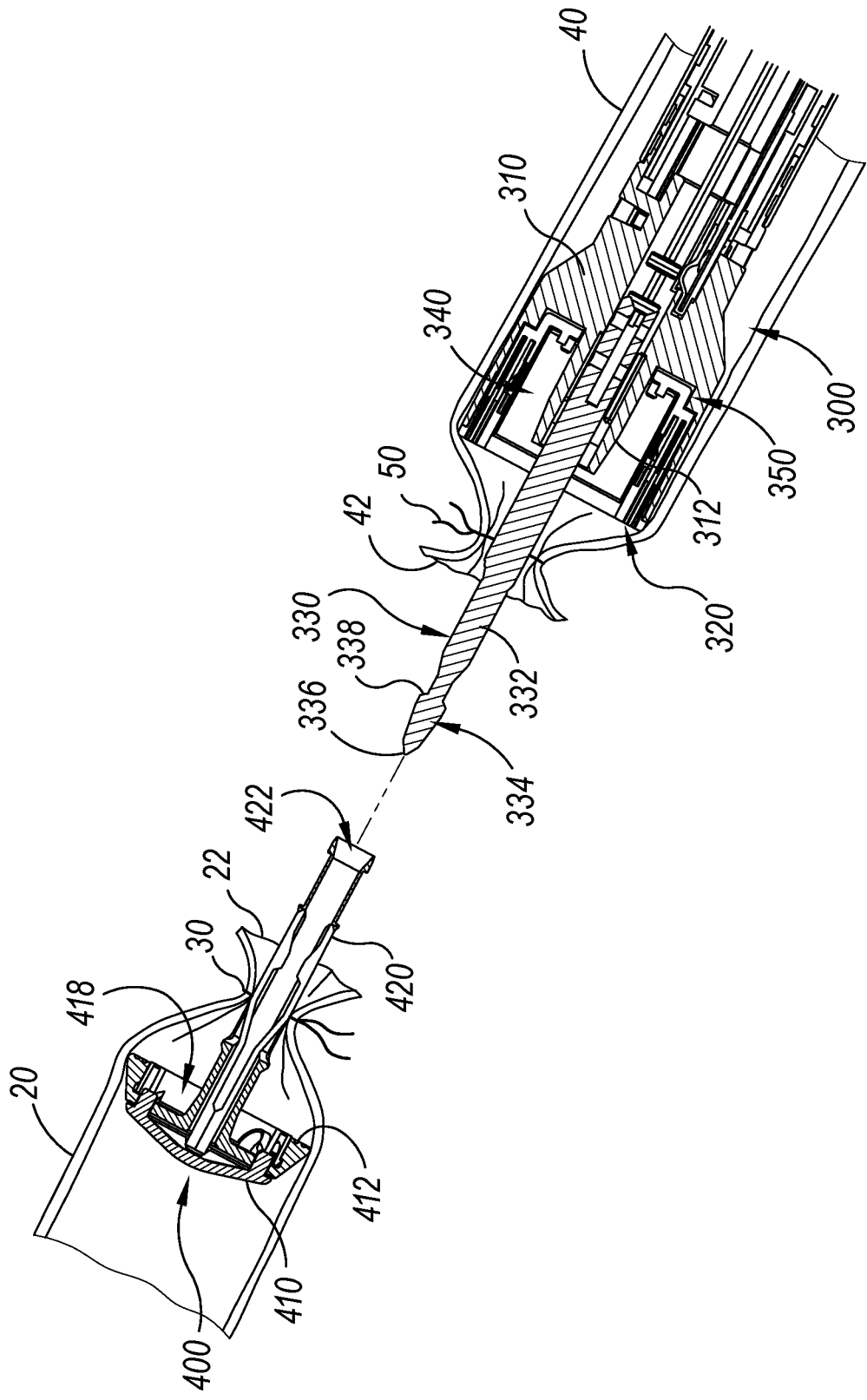
FIG. 7A depicts a cross-sectional side view of the anvil of FIG. 3 positioned within a first section of a digestive tract and the stapling head assembly of FIG. 4 positioned in a second section of the digestive tract, with the anvil separated from the stapling head assembly.

As shown in FIG. 7A, anvil (400) is positioned in one tubular anatomical structure (20) and stapling head assembly (300) is positioned in another tubular anatomical structure (40). In versions where tubular anatomical structures (20, 40) comprise sections of a patient's colon, stapling head assembly (300) may be inserted via the patient's rectum. It should also be understood that the procedure depicted in FIGS. 7A-7E is an open surgical procedure, though the procedure may instead be performed laparoscopically. Various suitable ways in which instrument (10) may be used to form an anastomosis (70) in a laparoscopic procedure will be apparent to those skilled in the art in view of the teachings herein.

As shown in FIG. 7A, anvil (400) is positioned in tubular anatomical structure (20) such that shank (420) protrudes from the open severed end (22) of tubular anatomical structure (20). In the present example, purse-string suture (30) is provided about a mid-region of shank (420) to generally secure the position of anvil (400) in tubular anatomical structure (20). In some other variations, purse-string suture (30) is tightened around the proximal end of shank (420). In some such variations, the proximal end of shank (420) may include a notch or other feature to securely capture purse-string suture (30). Continuing with the present example, stapling head assembly (300) is positioned in tubular anatomical structure (40) such that trocar (330) protrudes from the open severed end (42) of tubular anatomical structure (20). A purse-string suture (50) is provided about a mid-region of shaft (332) to generally secure the position of stapling head assembly (300) in tubular anatomical structure (40). Stapling head assembly (300) is then urged distally to ensure that stapling head assembly (300) is fully seated at the distal end of tubular anatomical structure (40).

Figure 7B:
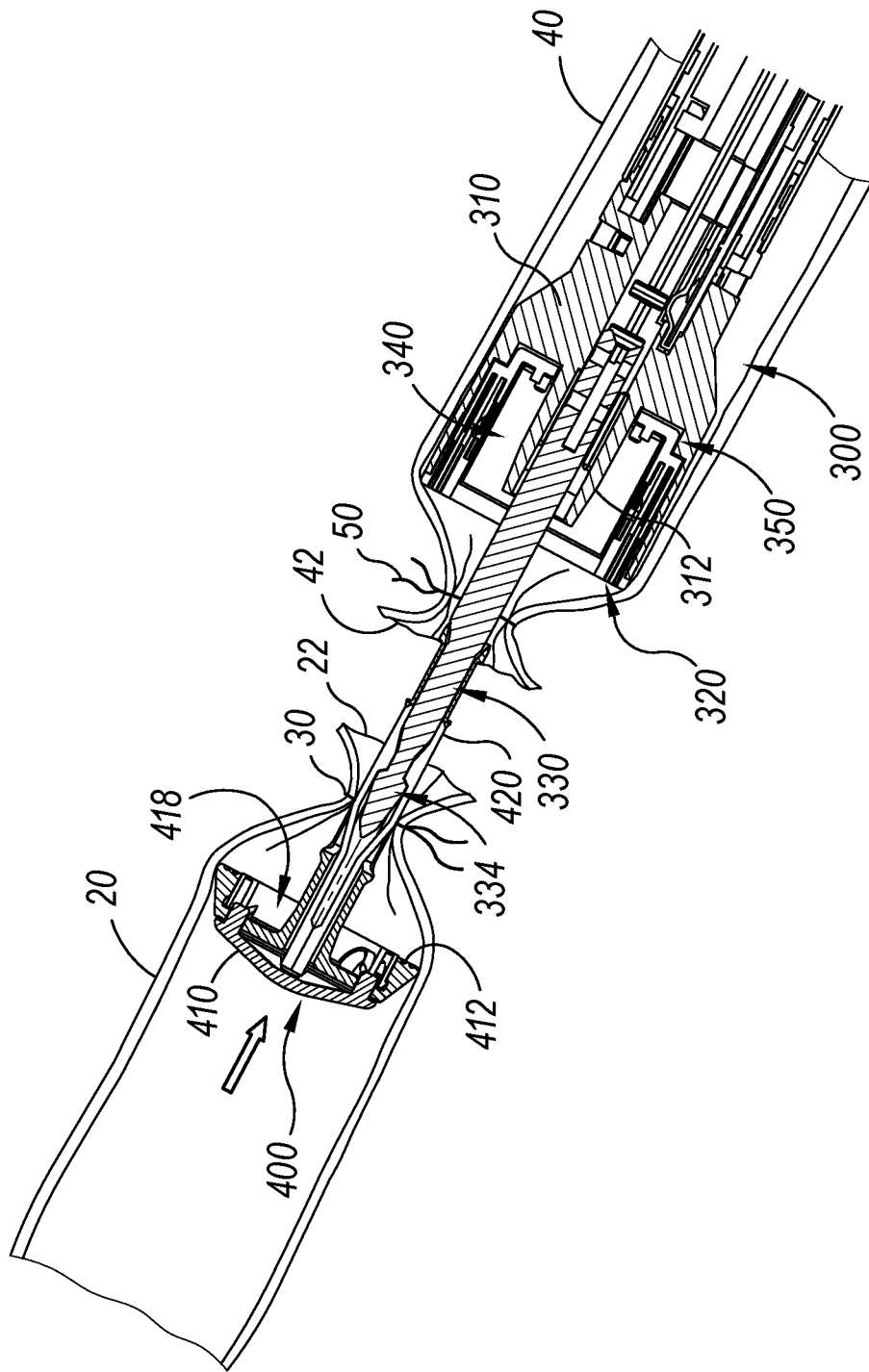
FIG. 7B depicts a cross-sectional side view of the anvil of FIG. 3 positioned within the first section of the digestive tract and the stapling head assembly of FIG. 4 positioned in the second section of the digestive tract, with the anvil secured to the stapling head assembly.
Figure 7C:
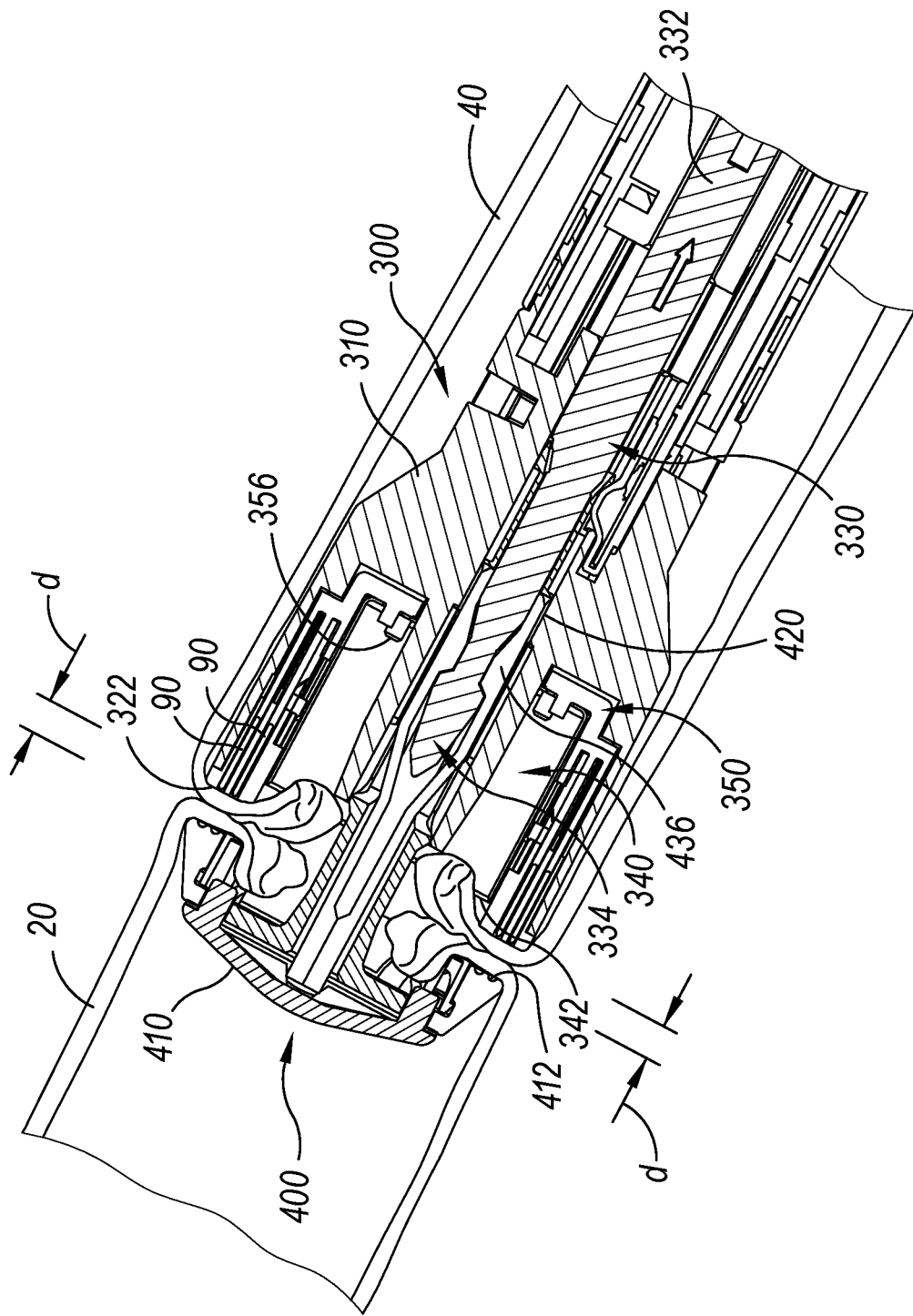
FIG. 7C depicts a cross-sectional side view of the anvil of FIG. 3 positioned within the first section of the digestive tract and the stapling head assembly of FIG. 4 positioned in the second section of the digestive tract, with the anvil retracted toward the stapling head assembly to thereby clamp tissue between the anvil and the stapling head assembly.

Next, anvil (400) is secured to trocar (330) by inserting trocar (330) into bore (422) as shown in FIG. 7B. Latch members (430) engage head (334) of trocar (330), thereby providing a secure fit between anvil (400) and trocar (330). The operator then rotates knob (130) while holding casing (110) stationary via pistol grip (112). This rotation of knob (130) causes trocar (330) and anvil (400) to retract proximally. As shown in FIG. 7C, this proximal retraction of trocar (330) and anvil (400) compresses the tissue of tubular anatomical structures (20, 40) between surfaces (412, 322) of anvil (400) and stapling head assembly (300). As this occurs, the operator may observe the tactile resistance or feedback via knob (130) while turning knob (130), with such tactile resistance or feedback indicating that the tissue is being compressed. As the tissue is being compressed, the operator may visually observe the position of an indicator needle (522) within a user interface feature (114) of handle assembly (100) to determine whether the gap distance (d) between opposing surfaces (412, 322) of anvil (400) and stapling head assembly (300) is appropriate; and make any necessary adjustments via knob (130).

Figure 7D:
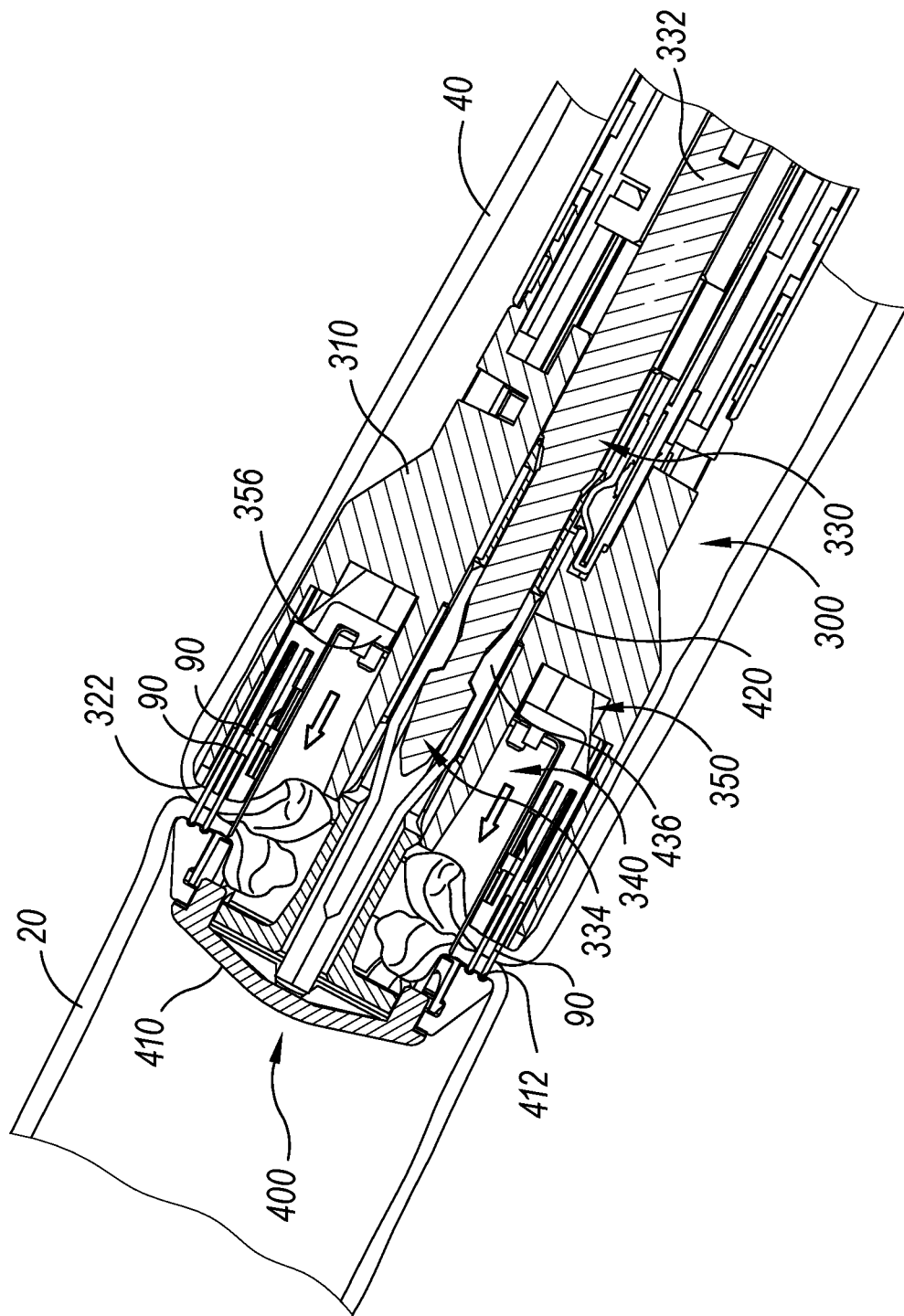
FIG. 7D depicts a cross-sectional side view of the anvil of FIG. 3 positioned within the first section of the digestive tract and the stapling head assembly of FIG. 4 positioned in the second section of the digestive tract, with the stapling head assembly actuated to sever and staple the clamped tissue.

Once the operator has appropriately set the gap distance (d) via knob (130), the operator pivots safety trigger (140) toward pistol grip (112) to enable actuation of firing trigger (150). The operator then pivots firing trigger (150) toward pistol grip (112), thus causing paddle (not shown) to actuate the switch of motor activation module (180) and thereby activate motor (160) to rotate. This rotation of motor (160) causes actuation (or "firing") of stapling head assembly (300) by actuating drive bracket (250) distally to thereby drive knife member (340) and staple driver member (350) distally, as shown in FIG. 7D. As knife member (340) translates distally, cutting edge (342) of knife member (340) cuts excess tissue that is positioned within annular recess (418) of anvil (400) and the interior of knife member (340).

As shown in FIG. 3, anvil (400) of the present example includes a breakable washer (417) positioned within annular recess (418). This washer (417) is broken by knife member (340) when the knife member (340) completes a full distal range of motion from the position shown in FIG. 7C to the position shown in FIG. 7D. Features of stapler (10) may be configured to provide an increasing mechanical advantage as knife member (340) reaches the end of its distal movement, thereby providing greater force by which to break the washer (417). Of course, the breakable washer (417) may be omitted entirely in some versions. In versions where washer (417) is included, it should be understood that washer (417) may also serve as a cutting board for knife member (340) to assist in cutting of tissue.

As staple driver member (350) translates distally from the position shown in FIG. 7C to the position shown in FIG. 7D, staple driver member (350) drives staples (90) through the tissue of tubular anatomical structures (20, 40) and into staple forming pockets (414) of anvil (400). Staple forming pockets (414) deform the driven staples (90) into a "B" shape or a three-dimensional shape, for example, such that the formed staples (90) secure the ends of tissue together, thereby coupling tubular anatomical structure (20) with tubular anatomical structure (40).

Figure 7E:
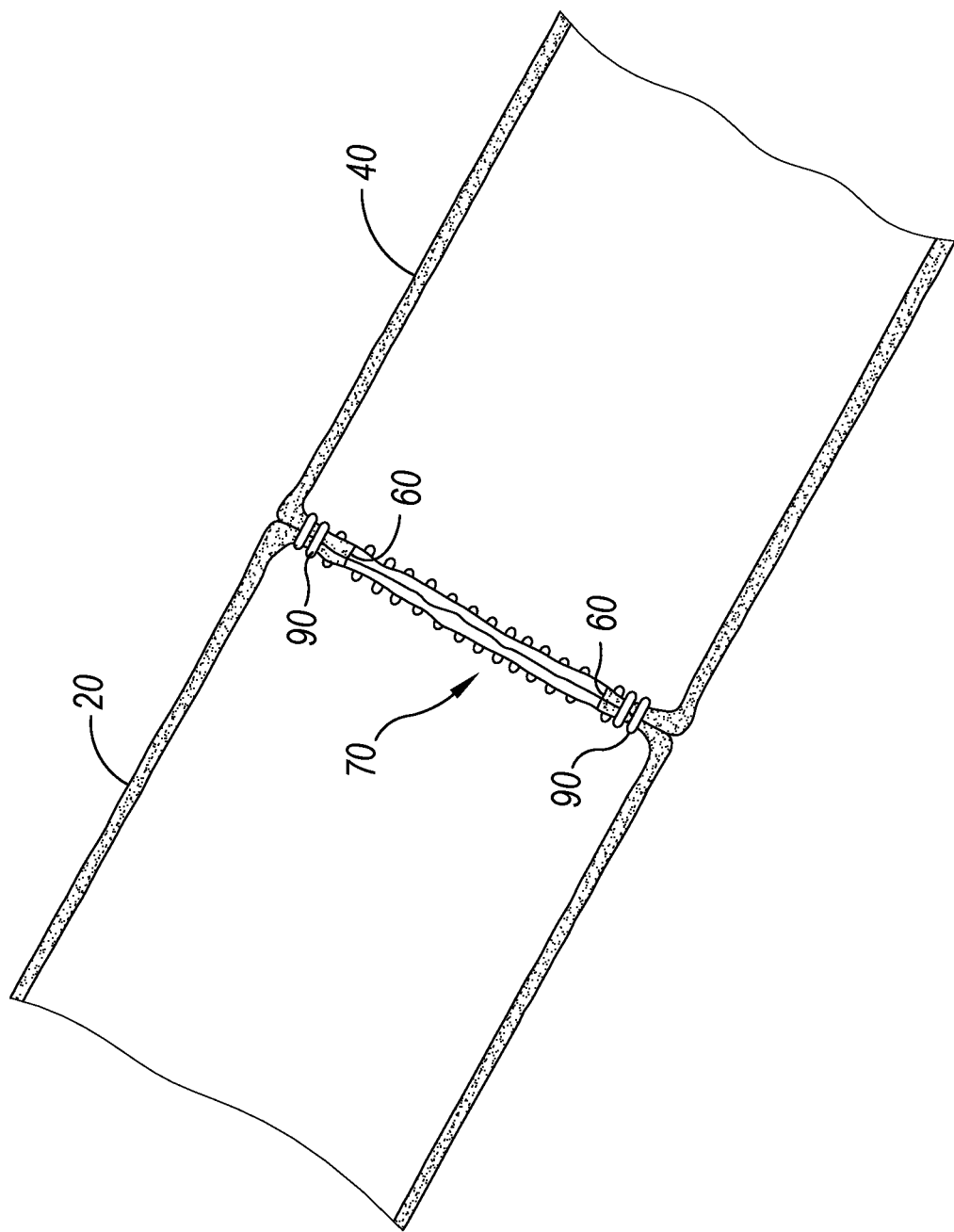
FIG. 7E depicts a cross-sectional side view of the first and second sections of the digestive tract of FIG. 7A joined together at an end-to-end anastomosis.
Figure 8:
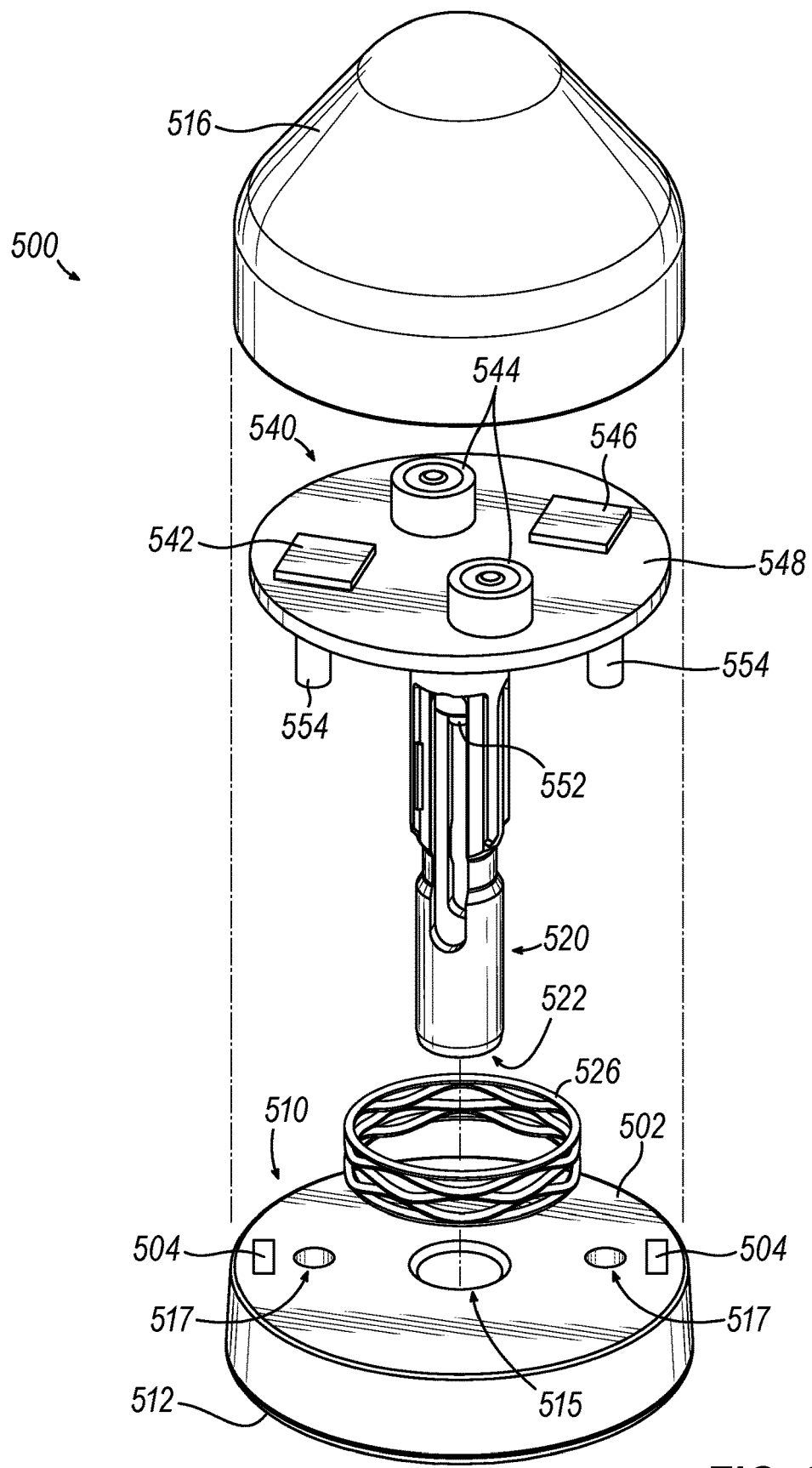
FIG. 8 depicts an exploded perspective view of an alternative anvil having a head, a shank, and a shroud that encloses certain electronic components of the anvil.
Figure 9:
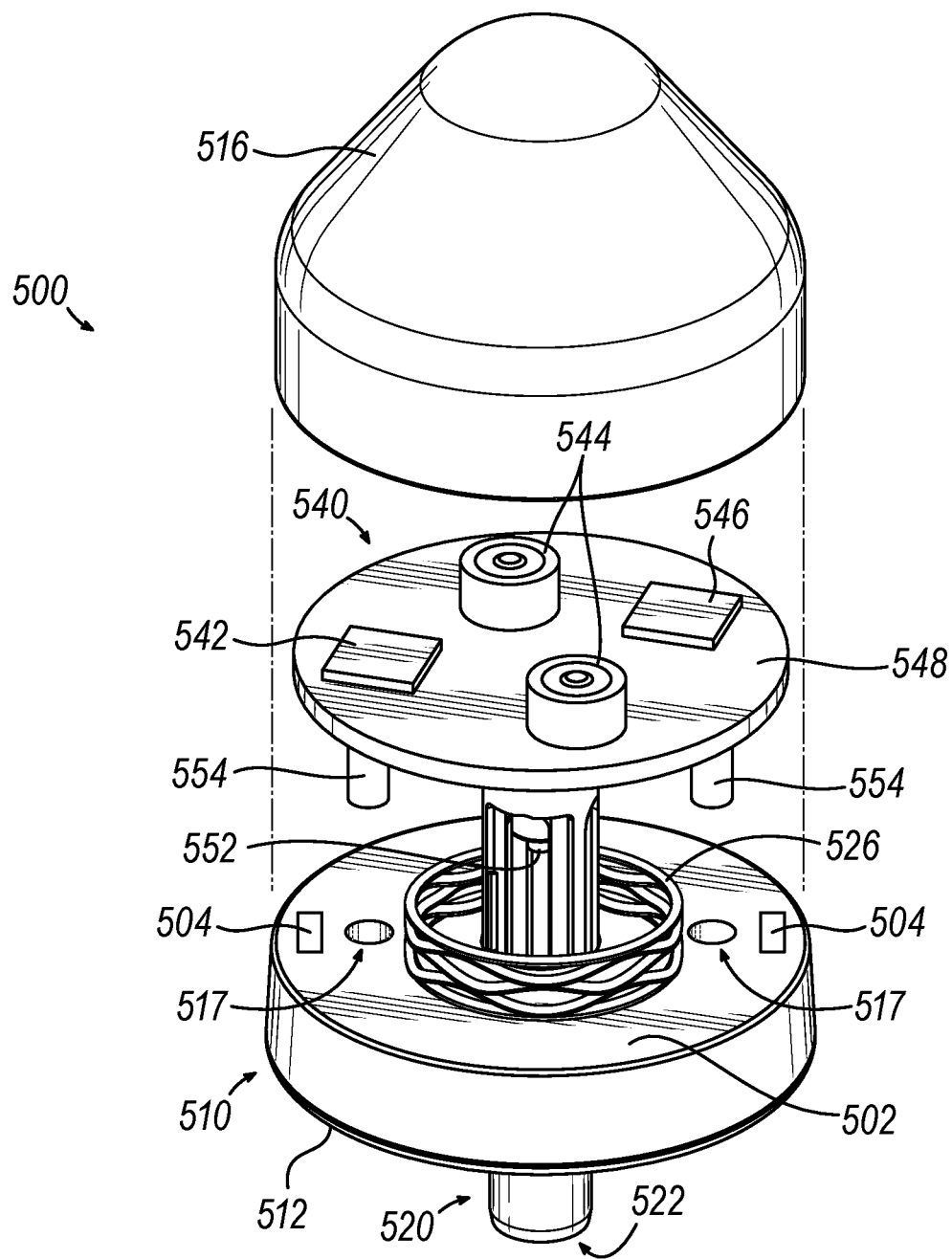
FIG. 9 depicts another exploded perspective view of the anvil of FIG. 8, with the shank partially inserted into a central through hole of the head.

After the operator has actuated stapling head assembly (300) as shown in FIG. 7D, the operator rotates knob (130) to drive anvil (400) distally away from stapling head assembly (300), increasing the gap distance (d) to facilitate release of the tissue between surfaces (412, 322). The operator then removes instrument (10) from the patient, with anvil (400) still secured to trocar (330). Referring back to the example where the tubular anatomical structures (20, 40) comprise sections of a patient's colon, instrument (10) may be removed via the patient's rectum. With instrument (10) removed, the tubular anatomical structures (20, 40) are left secured together by two annular arrays of staples (90) at an anastomosis (70) as shown in FIG. 7E. The inner diameter of the anastomosis (70) is defined by the severed edge (60) left by knife member (340).

II. Illustrative Wireless Powered Anvil and Method of Use

In certain situations, it may be beneficial to transmit tissue compression data and/or visual data from the anvil to a controller that may be housed within remaining portions of the surgical stapler or outside of the surgical stapler. Furthermore, it may also be beneficial to remotely transmit tissue compression data and/or visual data from the anvil to a control center or a receiver.

As mentioned above, some features provide a way to confirm that the anvil is connected with the trocar, and other features provide a way to gauge the degree of staple formation based on the distance between the underside anvil surface having the stapling forming pockets and the deck surface having the staple openings. In some instances, it would be separately or additionally desirable to have the ability to visually confirm, prior to firing or driving staples, that the trocar is suitably coupled with anvil and that tissue is suitably compressed between deck surface and the underside anvil surface. For example, in some instances, tissue may be interposed between trocar (330) and pivoting latch members (430) such that when pivoting latch members (430) provide tactile feedback via engagement with trocar (330), tissue is still interposed therebetween. In such instances, trocar (330) and pivoting latch members (430) may slip relative to each other as anvil (400) is actuated toward deck surface (320) in order to define a suitable gap distance therebetween while clamping tissue. As another example, in some instances, tissue located between proximal surface (412) of anvil (400) and deck surface (320) may not be in continuous annular engagement with surfaces (412, 320) with sufficient thickness (i.e. tissue is not interposed between portions of surfaces (412, 320) directly adjacent to each other while clamping tissue). In such instances, if the device is fired to staple and sever tissue, the recently formed anastomosis may have leaks due to gaps in grasped tissue and/or too think of tissue at certain locations.

In some instances, it may be desirable to confirm the tissue compression between surfaces (412, 320) has not deviated an undesirable amount from the moment a suitable gap distance was created and the moment device is fired to staple and sever tissue. In some instances, tissue grasped between surface (412, 320) may "milk" due to being exposed to compressive forces for a prolonged period of time, thereby loosing retained fluid. If grasped tissue looses too much fluid, the tissue compression forces may deviate from the moment the suitable gap distance was created, which could lead to less than desirable staple quality formation.

In some such situations, it may be desirable to utilize an anvil that is capable in the manner described above, and that is furthermore powered independently from the remainder of the circular stapler and is capable of wirelessly transmitting data to the controller, such that the anvil may be used with a variety of different circular staplers. FIGS. 8-10F show an illustrative alternative anvil that is configured and operable in such a manner, as described in greater detail below.

A. Wireless Powered Anvil

FIGS. 8-10F show an illustrative anvil (500) that is configured for use with instrument (10) and is substantially similar to anvil (400) and the anvils described in U.S. Pat. No. 11,490,891, which has been incorporated by reference above, except as otherwise described below. In some versions, anvil (500) may be used with stapling head assembly (300) in place of anvil (400).

Anvil (500) includes a head (510), a shank (520), a biasing element in the form of a multi-wave spring (526), and an electronic unit (540) associated with a portion of shank (520). As will be described in greater detail below, electronic unit (540) is configured to capture visual images while anvil (500) is being coupled to trocar (330) and actuated toward staple deck (320) to compress tissue against in accordance with the description herein; as well as communicate the captured visual images to a suitable controller (such as a surgeon's console having computing power and a display screen). Additionally, electronic unit (540), in conjunction with multi-wave spring (526), is configured to measure tissue compression imparted on grasped tissue by anvil (500) and staple deck (320) in accordance with the description herein; as well as communicate the measured tissue compression data to a suitable controller (such as a surgeon's console having computing power and a display screen).

Head (510) and shank (520) may be substantially similar to head (410) and shank (420) described above, with differences elaborated below. Head (510) includes a proximal surface (512) defining a plurality of staple forming pockets (514) (see FIGS. 10A-10F) and an annular recess (519); which may be substantially similar to proximal surface (412), staple forming pockets (414), and annular recess (418) described above, respectively, with differences elaborated herein. Therefore, proximal surface (512) of head (510) may be used in conjunction with staple deck (320) in order to suitable compress tissue; while staple forming pocket (514) may deform a generally "U" shaped staple into a "B" shaped staple. Head (510) also includes a distal surface (502). A shroud (516) is attached to head (510) in order to house spring (526) and electronic unit (540). Head (510) also defines a pair of lateral through holes (517) dimensioned to receive lateral camera (554) of electronics unit (540); and a central through hole (515) dimensioned to receive shank (520). Head (510) also includes a distal surface (502). Distal surface (502) and shroud (516) cooperatively define an interior (518) that slidably houses electronic unit (540).

Additionally, shank (520) defines a central bore (522), and a pair of lateral openings (524) which house a respective pivoting latch member (530) (see FIGS. 10A-10F); which may be substantially similar to bore (422), lateral openings (424), and pivoting latch members (430) described above, with differences elaborated herein. Therefore, central bore (522) may receive trocar (330) while pivoting latch member (530) may act as retaining clips to allow anvil (500) to be removably secured to trocar (330).

Spring (526) is interposed between head (510) and shank (520) and such that head (510) and shank (520) may translate relative to each other along the longitudinal axis (LA) (see FIG. 9) of anvil (500). Ends of spring (526) are fixed to respective portions of head (510) and shake (520) such translation of head (510) and shank (520) relative to each other drives compression and/or expansion of spring (526) from its resting length. Spring (526) is coupled to head (510) and shank (520) via any suitable as would be apparent to one skilled in the art in view of the teachings herein. For example, ends of spring (526) may be welded to respective portions of head (510) and shank (520).

Spring (526) has a known spring constant such that the change in the length of spring (526) from its resting length is indicative of a force acting on spring (526). Since spring (526) couples shank (520) to head (510), as shank (520) is pulled proximally via trocar (330) in order to drive proximal surface (512) of head (510) to clamp tissue against deck member (320) in accordance with the description herein, clamped tissue imparts a reactionary force onto head (510), which may in turn drive translation of head (510) relative to shank (520). The reactionary force provided by clamped tissue is indicative of the tissue compression force which head (510) and deck member (320) impart on grasped tissue.

With the known spring constant of spring (526), the distance head (510) moves relative to shank (520) while grasping tissue can be utilized in order to calculate the compression force which head (510) and deck member (320) impart on grasped tissue. As mentioned above, if tissue is clamped between head (510) and deck member (320) for a prolonged period of time, retained fluids within tissue may begin to "milk" and escape from clamp tissue. Such milking of tissue may lead to a reduction in tissue compression force imparted by head (510) and deck member (320) onto tissue. A reduction in tissue compression force causes spring (526) length to increase. As will be described in greater detail below, electronic unit (520) is configured to measure these changes in distance between head (510) and shank (520) in order to provide the ability to calculate the tissue compression force via the known spring constant of spring (526).

Electronic unit (540) is attached to shank (520) and housed within an interior recess (518) defined by a shroud (516) fixed to head (510). Therefore, as shank (520) actuates relative to head (510) in accordance with the description here, so does electronic unit (540). Electronic unit (540) includes control unit (542), a wireless transmitter (544), a battery (546), a base (548), at least one distance sensor (550) (see FIGS. 10A-10F), a bore camera (552), and a pair of lateral cameras (554). Control unit (542), wireless transmitter (544) and battery (546) are each in suitable communication with each other.

Battery (546) is configured to electrically power the necessary components of electronic unit (540), such as cameras (552, 554), distance sensor(s) (550), wireless transmitter (544), and control unit (542). Battery (546) may include any suitable components as would be apparent to one skilled in the art in view of the teachings herein. In some instances, battery (546) may be connected to a switch (or other suitable mechanism) configured to selectively activate battery (546) such that a user may selectively activate electronic unit (540). Such a switch may be present on the outer surface of shroud (516) or any other suitable location. Therefore, a user may activate electronic unit (540) prior to illustrative use. Of course, battery (546) may be configured to activate electronic unit (540) in response to any other suitable activation method as would be apparent to one skilled in the art in view of the teachings herein.

Control unit (542) is configured to suitably process the data from cameras (552, 554) and distance sensor(s) (550) in accordance with the description herein, while wireless transmitter (544) is configured to suitably transmit information (e.g., visual images, change in length of spring (526), tissue compression between proximal surface (512) and deck member (520), etc.) between control unit (542) and a suitable controller (such as a surgeon's console having computing power and a display screen). Control unit (542) and wireless transmitter (544) include any suitable electrical components necessary to perform the recited functions herein. Control unit (542) may include printed circuit board (PCB), suitable memory, and/or suitable processing means to function in accordance with the description herein. Wireless transmitter (544) may include a Bluetooth transmitter, wi-fi, or any other suitable wireless technology as would be apparent to one skilled in the art in view of the teachings herein.

As best shown in FIGS. 10A-10F, distance sensor(s) (550) is located on an underside of base (548) such that distance sensor(s) (550) faces toward distal surface (502) of head (510). Distal surface (502) of head includes at least one datum (504) that is aligned with a repetitive distance sensor (550). Distance sensor (550) is configured to measure a distance between itself and datum (504) of distal surface (502). Therefore, distance sensor (550) is configured to measure relative movement between head (510) and shank (520). As mentioned above, the distance between head (510) and shank (520) may be utilized in order to determine the tissue compression forces imparted on grasped tissue between proximal surface (512) and deck member (320) via the known spring constant of spring (526). Therefore, the measurement of distance sensor (550) may be utilized in order to determine the tissue compression forces imparted on grasped tissue.

Distance sensor (550) is configured to communicate this measurement to control unit (542), which may suitably process the measurement and transmit the processed measurement to wireless transmitter (544). In some instances, control unit (542) has a stored value of the spring constant of spring (526) and is configured to calculate a tissue compression profile based on the length of spring (526) and the spring constant. Wireless transmitter (544) is configured to send the processed measurement to a suitable controller (such as a surgeon's console having computing power and a display screen); which may then further process the measurement in order to display or otherwise communicate the tissue compression data based on the length of spring (526) and the spring constant, thereby enabling the user to make informed decisions in preparation of firing device (10).

Distance sensor (550) and datum (504) may include any suitable components as would be apparent to one skilled in the art in view of the teachings herein. For example, distance sensor (550) may be a Hall effector sensor, while datum (504) may be a magnet. As another example distance sensor (550) may be a light sensor, while datum (504) is a reflective surface.

Central camera (552) extends from the underside of base (548) and is located within central bore (522) of shank (522). Central camera (552) is configured to capture images of objects located within and extending away from central bore (522). Camera (552) is in communication with control unit (542) such that control unit (542) suitably processes the images and transmits the processed images to wireless transmitter (544). Wireless transmitter (544) is configured to send the processed images to a suitable controller (such as a surgeon's console having computing power and a display screen); which may then further process the images in order to display said images on a display screen. Central camera (552) may include a light source configured to illuminate objects within the images captured from camera (552).

A user may utilize images captured from camera (552) in order to ensure pivoting latch members (530) are suitably coupled to trocar (330) during illustrative use. Images from camera (552) may help assist a user in docking trocar (330) with shank (520). Additionally, a user may confirm tissue or other objects are not interposed between pivoting latch members (530) and trocar (330) once coupled together. Therefore, a user may visually confirm coupling between latch members (530) and trocar (330); rather than merely relying on audible/tractile feedback provided by latch members (530) engaging trocar (330).

Lateral cameras (554) also extend from the underside of base (548) and are located within a respective lateral through hole (517) defined by head (510). Lateral camera (554) is configured to capture images of objects located adjacent to deck member (320) while anvil (500) is coupled to trocar (330) in accordance with the description herein. Cameras (554) ire in communication with control unit (542) such that control unit (542) suitably processes the images and transmits the processed images to wireless transmitter (544). Wireless transmitter (544) is configured to send the processed images to a suitable controller (such as a surgeon's console having computing power and a display screen); which may then further process the images in order to display said images on a display screen.

During illustrative use, lateral cameras (554) are configured to capture the annular portion of deck member (320) intended to engage tissue in order to suitably perform an fluid tight anastomosis. Therefore, a user may confirm enough tissue is placed between deck member (320) and proximal surface (512) in order to form a suitable anastomosis.

Cameras (554) include a light source configured to illuminate tissue resting on deck member (320) during illustrative use. Light illuminated from cameras (554) may be strong enough to transilluminate thin portions of tissue, thereby allowing a user to identify thin portions of tissue resting on deck member (320). Such thin portions of tissue may be susceptible to not forming a fluid tight anastomosis, as the thin tissue may damage easily after stapling and severing. Therefore, light emitted from cameras (554) may allow a user adjust tissue placement between deck member (320) and proximal surface (512) in order to help promote an appropriate tissue thickness.

Figure 10A:
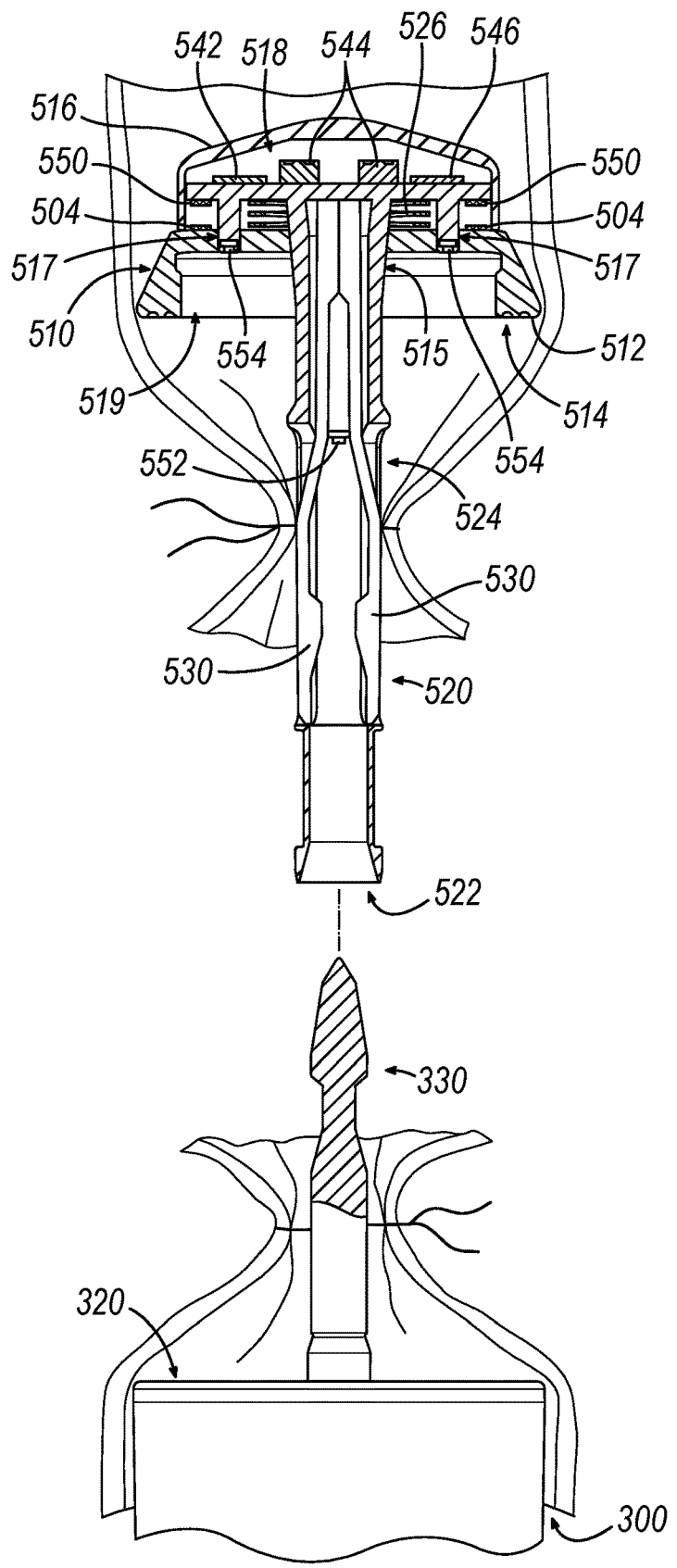
FIG. 10A depicts a cross-sectional side view of the anvil of FIG. 8 positioned within a first section of a digestive tract and the stapling head assembly of FIG. 4 positioned in a second section of the digestive tract, with the anvil separated from the stapling head assembly.
Figure 10B:
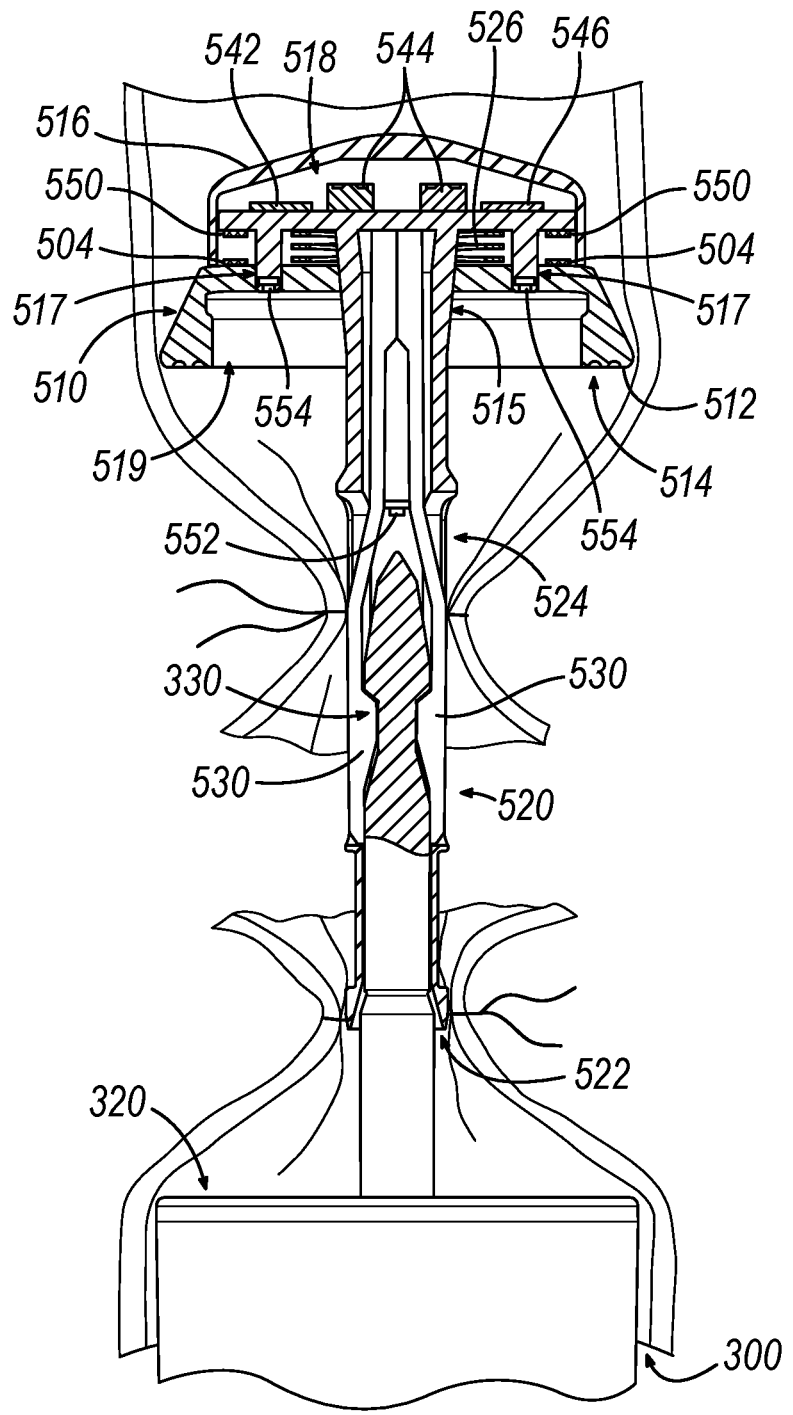
FIG. 10B depicts a cross-sectional side view of the anvil of FIG. 8 positioned within the first section of the digestive tract and the stapling head assembly of FIG. 4 positioned in the second section of the digestive tract, with the anvil secured to the stapling head assembly.

FIGS. 10A-10F show an illustrative use of anvil (500) with staple heard assembly (300) in order to perform an anastomosis. First, as shown in FIG. 10A, anvil (500) may be aligned with trocar (330) such that central bore (522) is placed adjacent to trocar (330). Central camera (552) may be utilized in order to assist in aligning central bore (522) with trocar (330). Next, as shown in FIG. 10B, trocar (330) may be inserted within central bore (522) such that pivoting latch members (530) suitably engage trocar (330). Central camera (552) may be utilized in order to visually confirm no tissue is interposed between trocar (330) and pivoting latch member (530).

Figure 10C:
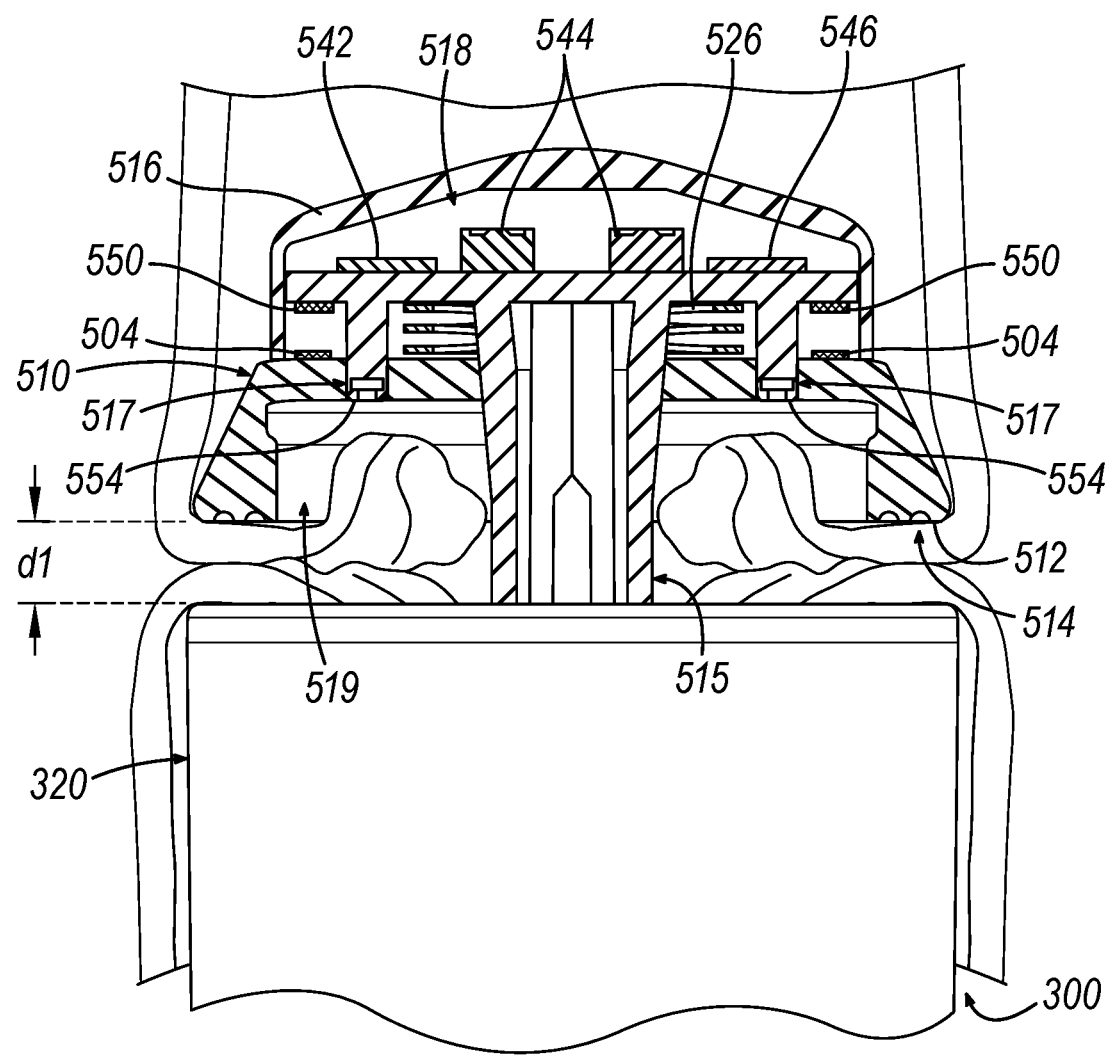
FIG. 10C depicts a cross-sectional side view of the anvil of FIG. 8 positioned within the first section of the digestive tract and the stapling head assembly of FIG. 4 positioned in the second section of the digestive tract, with the anvil retracted toward the stapling head assembly to thereby clamp tissue between the anvil and the stapling head assembly.
Figure 10D:
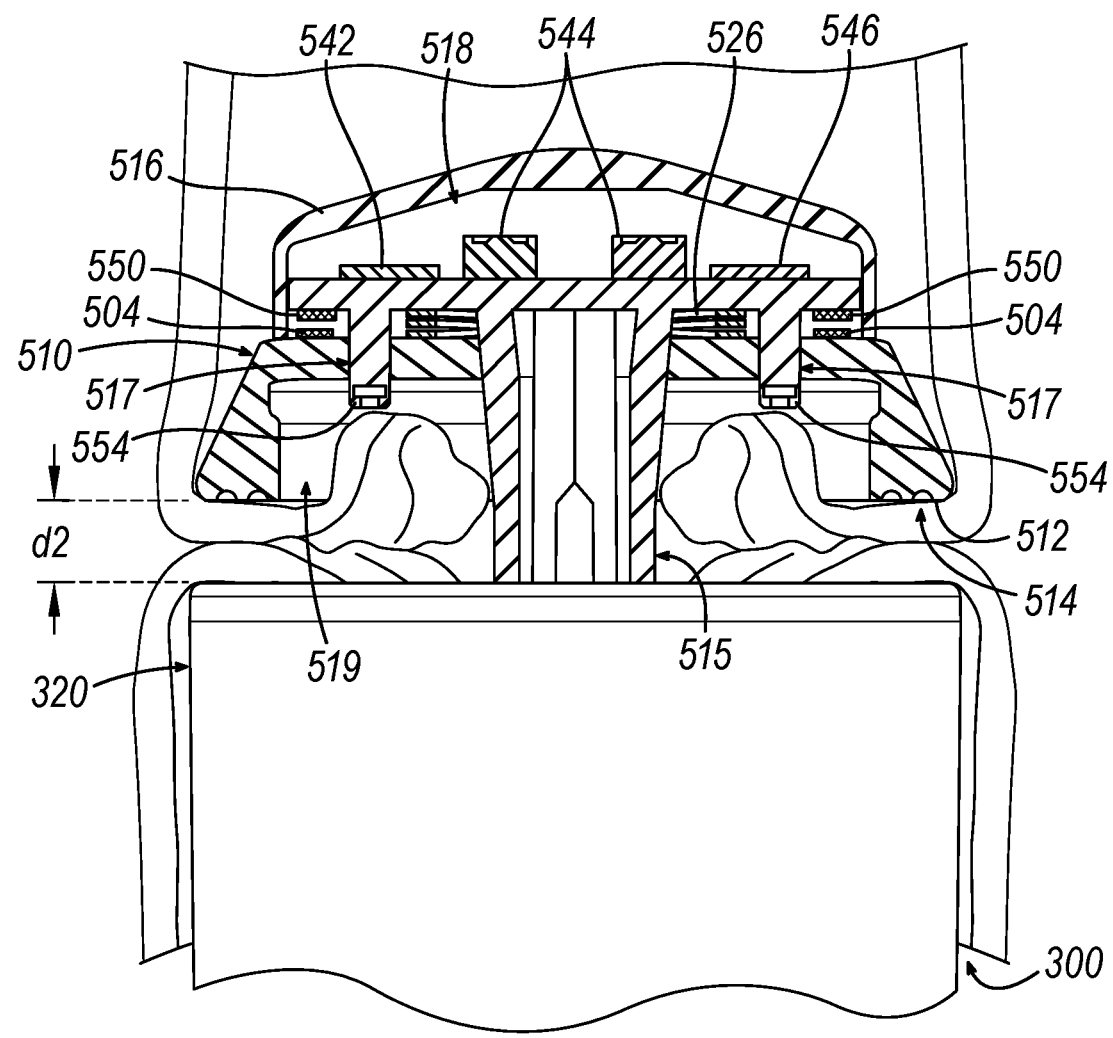
FIG. 10D depicts a cross-sectional side view of the anvil of FIG. 8 positioned within the first section of the digestive tract and the stapling head assembly of FIG. 4 positioned in the second section of the digestive tract, with the shank of the anvil actuated proximally relative to the head of the anvil, thereby compressing a spring interposed therebetween.

Next, as shown in FIGS. 10C-10D, a user may actuate anvil (500) proximally toward deck member (320) such that proximal surface (512) and deck member (320) clamps tissue with an increasing clamping force. It should be understood that spring (526) compresses as the clamping forces increases. Distance sensor (550) detect the compression of spring (526) in accordance with the description herein, and control unit (542) utilizes the known spring constant of spring (526) in order to determine the tissue compression forces which anvil (500) and deck member (320) impart on grasped tissue. The tissue compression forces may be communicated to a user via wireless transmitter (544) in accordance with the teachings herein. In some instances, the gap distance (d1) shown in FIG. 10C remains the same as the gap distance (d2) shown in FIG. 10D. In other instances the gap distances (d1, d2) also change as clamping forces increase.

Figure 10E:
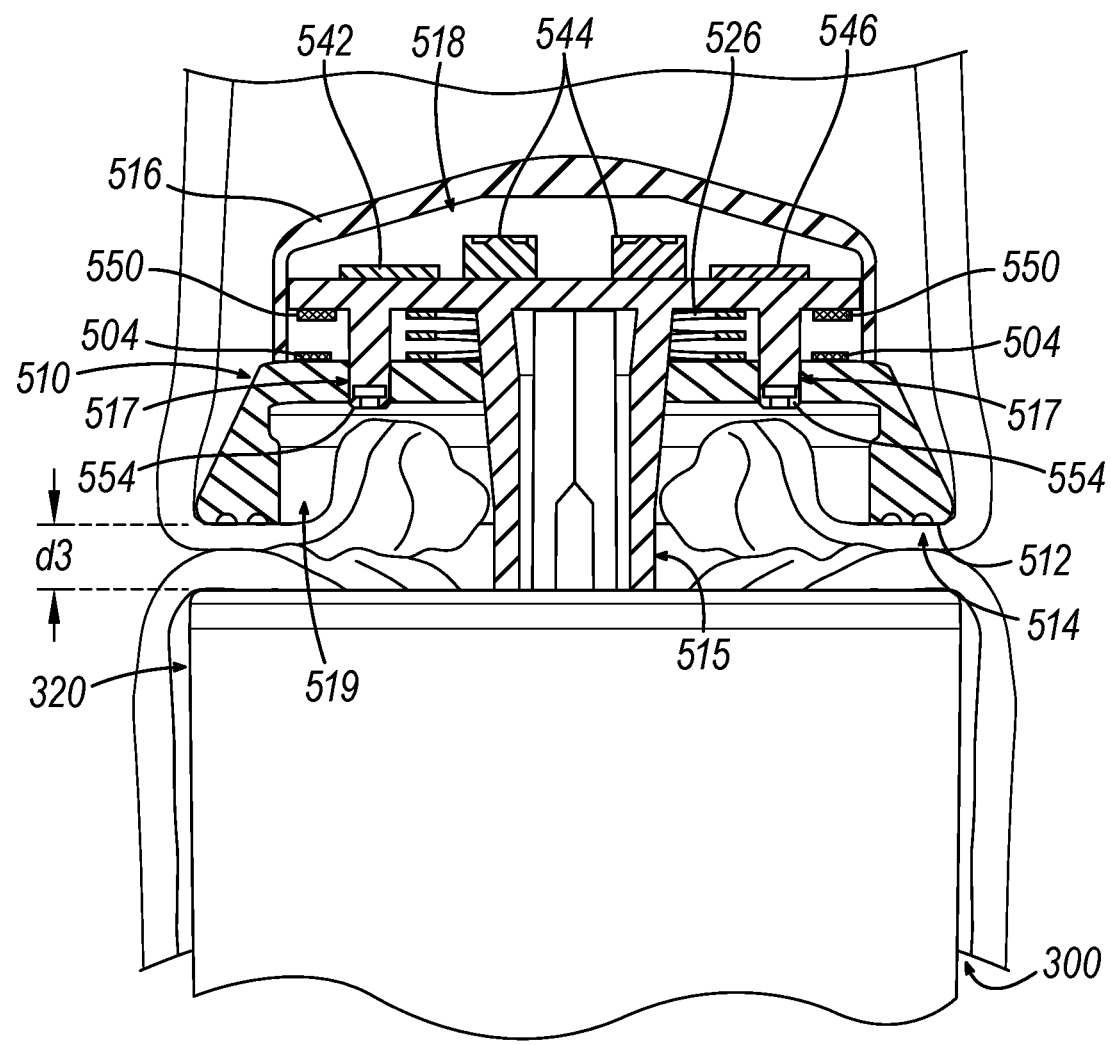
FIG. 10E depicts a cross-sectional side view of the anvil of FIG. 8 positioned within the first section of the digestive tract and the stapling head assembly of FIG. 4 positioned in the second section of the digestive tract, with the spring of FIG. 10D expanding thereby driving shank of the anvil distally relative to the head of the anvil.

In some instances, as shown in FIGS. 10D-10E, the tissue compression forces may decrease due to a milking effect. In such instances, the tissue compression forces may decrease, thereby allowing spring (526) to elongate as shown in FIG. 10E, creating a smaller clamp distance (d3). Distance sensor (550) detects the elongation of spring (526) in accordance with the description herein, and control unit (542) utilizes the known spring constant of spring (526) in order to determine the new tissue compression forces which anvil (500) and deck member (320) impart on grasped tissue. A user may make necessary adjustments prior to firing based on this information.

Figure 10F:
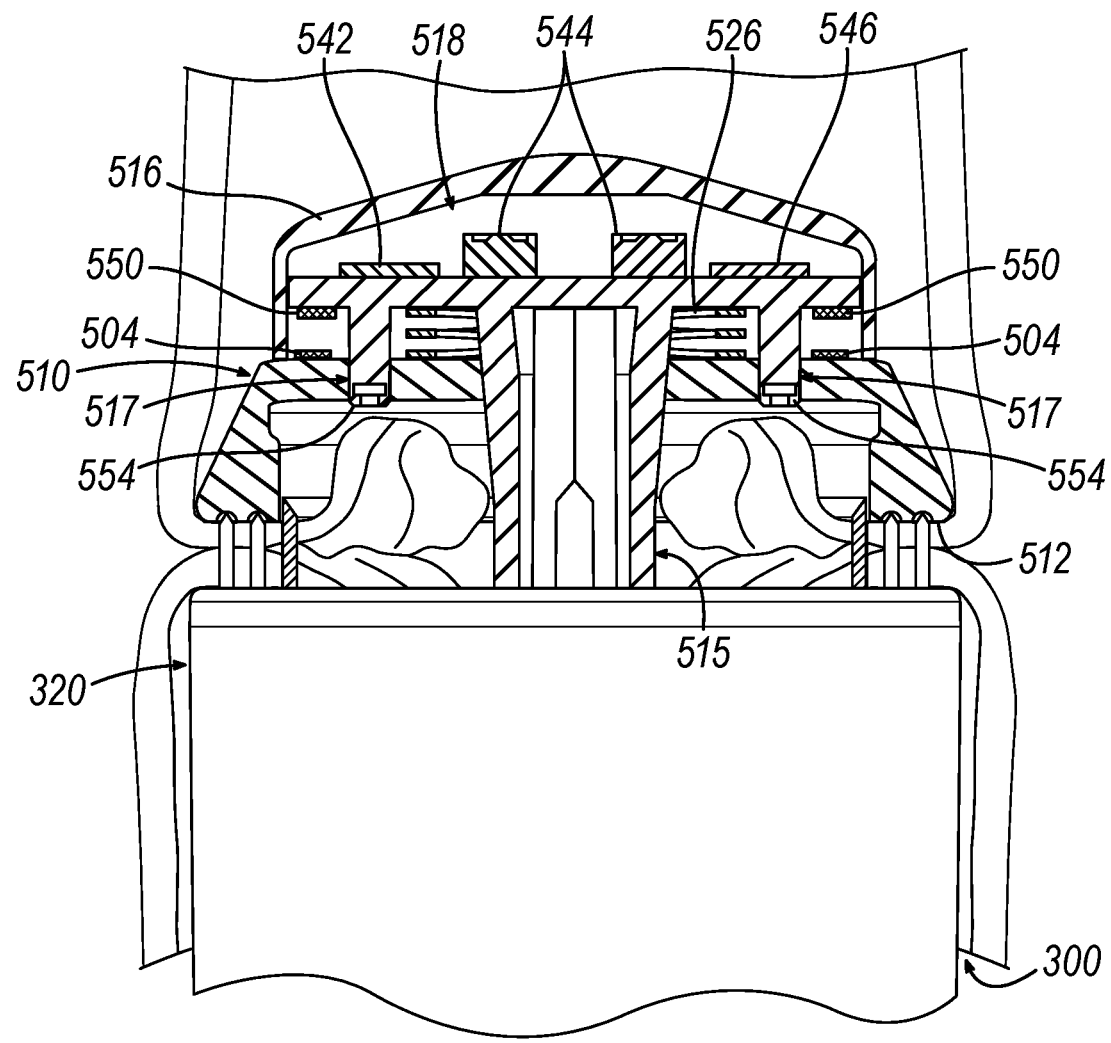
FIG. 10F depicts a cross-sectional side view of the anvil of FIG. 8 positioned within the first section of the digestive tract and the stapling head assembly of FIG. 4 positioned in the second section of the digestive tract, with the stapling head assembly actuated to sever and staple the clamped tissue.

Next, as shown in FIG. 10F, a user may fire staples and sever tissue in accordance with the description herein. Further, the user may remove both anvil (500) and staple head assembly (300), thereby leaving a completed anastomosis.

Figure 11:
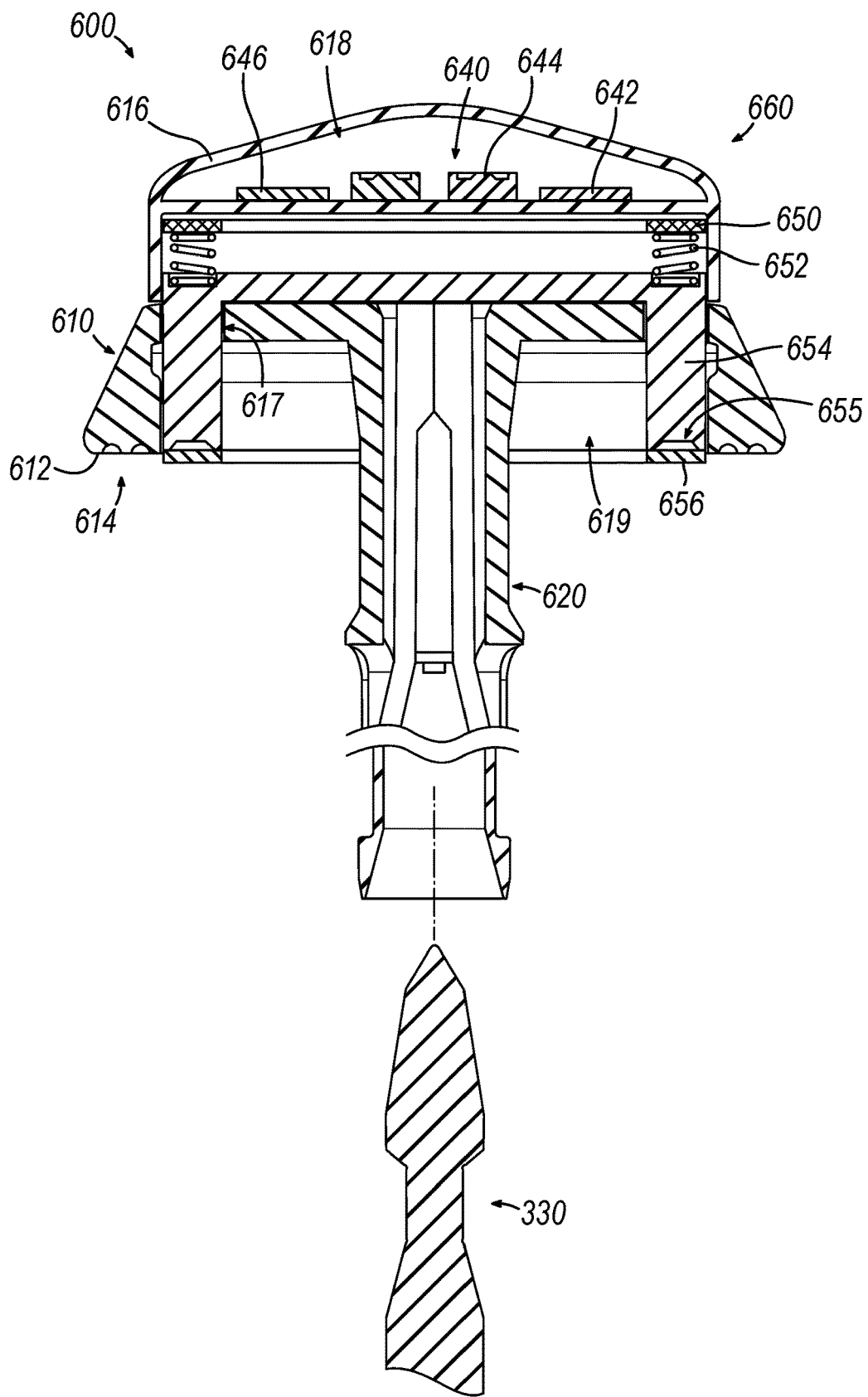
FIG. 11 depicts a cross-sectional side view of an alternative anvil having a head, a shank, a shroud that encloses certain electronic components of the anvil, and a pressure measuring assembly.

FIG. 11 shows an illustrative anvil (600) that may be used with instrument (10) in replacement of anvil (400, 500)

described above. Therefore, anvil (600) may be substantially similar to anvil (400, 500) described above, with differences elaborated herein.

Anvil (600) includes a head (610), a shank (620), a tissue load measuring assembly (660), and an electronic unit (640). As will be described in greater detail below, electronic unit (640), in conjunction with tissue load measuring assembly (660), is configured to measure tissue force, pressure, and/or loads imparted on grasped tissue by anvil (600) and staple deck (320) in accordance with the description herein; as well as communicate the measured tissue force, pressure, and/or loads data to a suitable controller (such as a surgeon's console having computing power and a display screen).

Head (610) and shank (620) may be substantially similar to head (410) and shank (420) described above, with differences elaborated below. Head (610) and shank (620) are fixed to each other in the current example. Head (610) includes a proximal surface (612) defining a plurality of staple forming pockets (614) and an annular recess (619); which may be substantially similar to proximal surface (412, 512), staple forming pockets (414, 514), and annular recess (418, 519) described above, respectively, with differences elaborated herein. Therefore, proximal surface (612) of head (610) may be used in conjunction with staple deck (320) in order to suitable compress tissue; while staple forming pocket (614) may deform a generally "U" shaped staple into a "B" shaped staple. A shroud (616) is attached to head (610) in order to house electronic unit (640). Head (610) also defines a pair of lateral through holes (617) dimensioned to slidably receive a translating body (654) of tissue compression measuring assembly (660).

Additionally, shank (620) defines a central bore (622), and a pair of lateral openings (624) which house a respective pivoting latch member (630) (see FIGS. 10A-10F); which may be substantially similar to bore (422, 522), lateral openings (424, 524), and pivoting latch members (430, 530) described above, with differences elaborated herein. Therefore, central bore (622) receive trocar (330) while pivoting latch member (630) act as retaining clips to allow anvil (600) to be removably secured to trocar (330).

Electronic unit (640) is attached to shroud (616) within interior recess (618). Electronic unit (640) includes control unit (642), a wireless transmitter (644), a battery (646); which may be substantially similar to control unit (542), wireless transmitter (544), and battery (546) described above, with differences elaborated below. Therefore, battery (646) is configured to electrically power the necessary components of electronic unit (640) as well as necessary components of tissue load measuring assembly (660).

Control unit (642) is in communication with a sensor (650) of tissue load measuring assembly (660) such that control unit (642) is configured to receive measurements from sensor (650) during illustrative use. Control unit (642) is configured to suitably process the data from sensor (650) in accordance with the description herein, while wireless transmitter (644) is configured to suitably transmit information (e.g., measurements from sensor (650), etc.) between control unit (642) and a suitable controller (such as a surgeon's console having computing power and a display screen).

Figure 12:
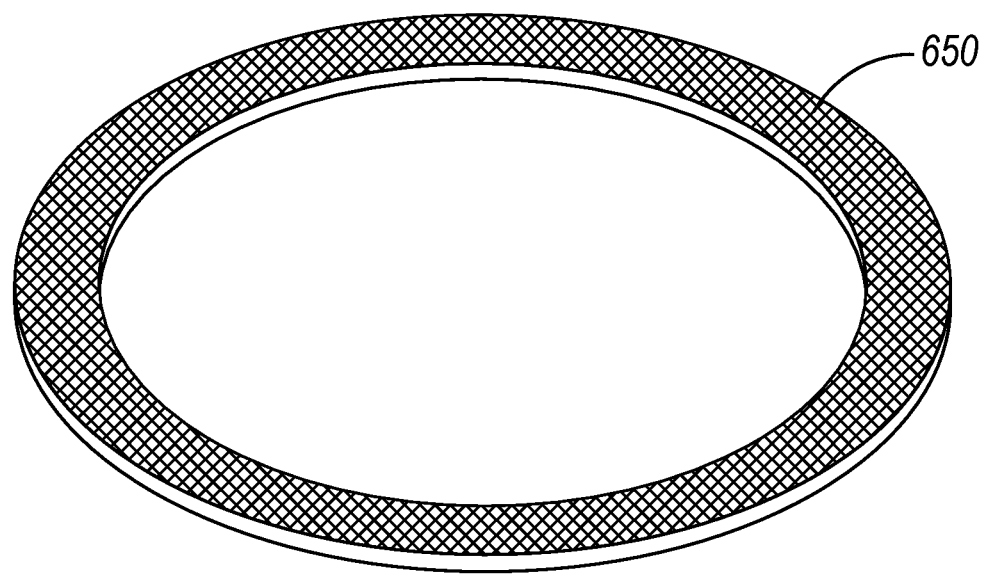
FIG. 12 depicts a perspective view of a pressure sensor of the pressure measuring assembly of FIG. 11.

Tissue load measuring assembly (660) includes sensor (650), a spring (652) extending proximally for pressure sensor (650), a translating body (654) attached to spring (652) and slidably disposed within lateral through holes (617) of head (610), and a breakaway washer (656) attached to a proximal end of translating body (654). Sensor (650) is configured to measure a force imparted on sensor (650) via spring (652) and communicate that measurement to control unit (642). As shown in FIG. 12, sensor (650) in the current example has an annular shape and may measure different forces along different regions of the annular shape. As will be described in greater detail below, forces imparted on sensor (650) via spring (652) are indicative of the forces imparted on tissue grasped between anvil (600) and deck member (520). Sensor (650) may be any suitable type of sensor as would be apparent to one skilled in the art in view of the teachings herein. For example, sensor (650) may be a strain gauge, a pressure gauge, a force transducer, a displacement gauge, a magnetic sensor, an electromagnetic sensor, a resistor, etc.

Spring (652) is interposed between sensor (650) and translating body (654). Spring (652) biases translating body (654) toward the position shown in FIG. 11 such that breakaway washer (656) is proximal in relation to proximal surface (612) of head (610). Therefore, as anvil (610) grasps tissue in conjunction with deck member (320) in accordance with the description herein, breakaway washer (656) engages tissue. Translating body (654) is configured to translate relative to head (610) along a path defined by through holes (617). Translating body (654) is configured to translate relative to head (610) in response to forces generated from breakaway washer (656) engaging tissue while proximal surface (612) of head (610) and deck member (320) clamp tissue in accordance with the description herein. Such movement of translating body (652) compresses spring (652), which in turn imparts a force, load, and/or pressure onto sensor (650) (which may be measured by sensor (650)) that is proportional to the compression which breakaway washer (656) imparts on tissue. The measurements from sensor (650) in response to breakaway washer (656) engaging tissue can be utilized in order to calculate the compression force, load, and/or pressure profile which head (610) and deck member (320) impart on grasped tissue. Such information may be transmitted to a suitable controller (such as a surgeon's console having computing power and a display screen) and displayed to user, thereby enabling the user to make informed decisions in preparation of firing device (10).

As mentioned above, if tissue is clamped between head (610) and deck member (320) for a prolonged period of time, retained fluids within tissue may begin to "milk" and escape from clamp tissue. Such milking of tissue may lead to a reduction in tissue compression force imparted by head (610) and deck member (320) onto tissue. A reduction in tissue compression force causes spring (652) length to increase as well as the measured compression force, load, and/or pressure profile to decrease. Sensor (650) may measure such reductions in compression force, load, and/or pressure profile and communicate that measurement to electronic unit (640); which in turn may communicate such measurements to a suitable controller (such as a surgeon's console having computing power and a display screen), thereby enabling the user to make informed decisions in preparation of firing device (10).

Figure 13A:
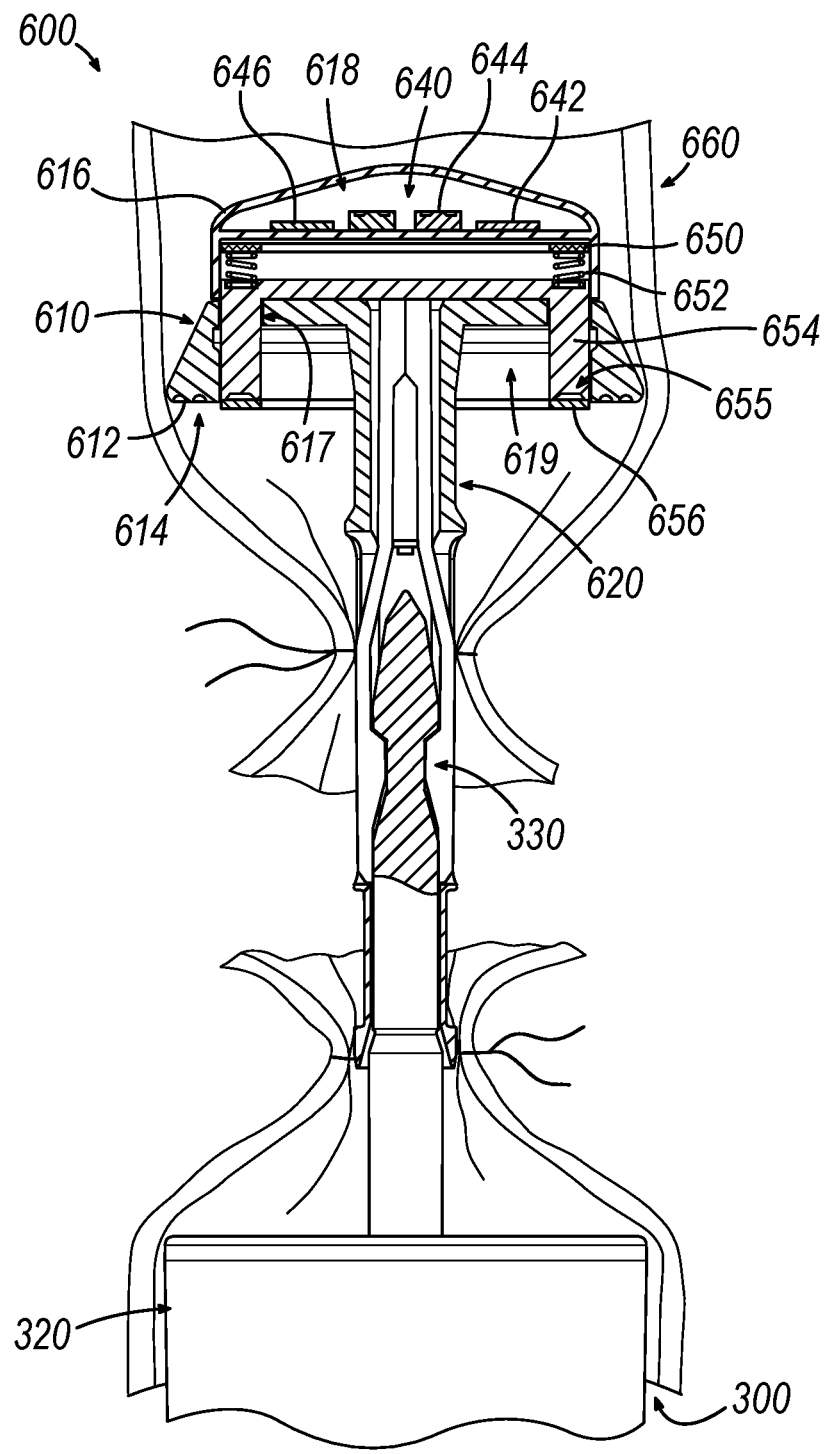
FIG. 13A depicts a cross-sectional side view of the anvil of FIG. 11 positioned within a first section of a digestive tract and the stapling head assembly of FIG. 4 positioned in a second section of the digestive tract, with the anvil secured to the stapling head assembly.
Figure 13B:
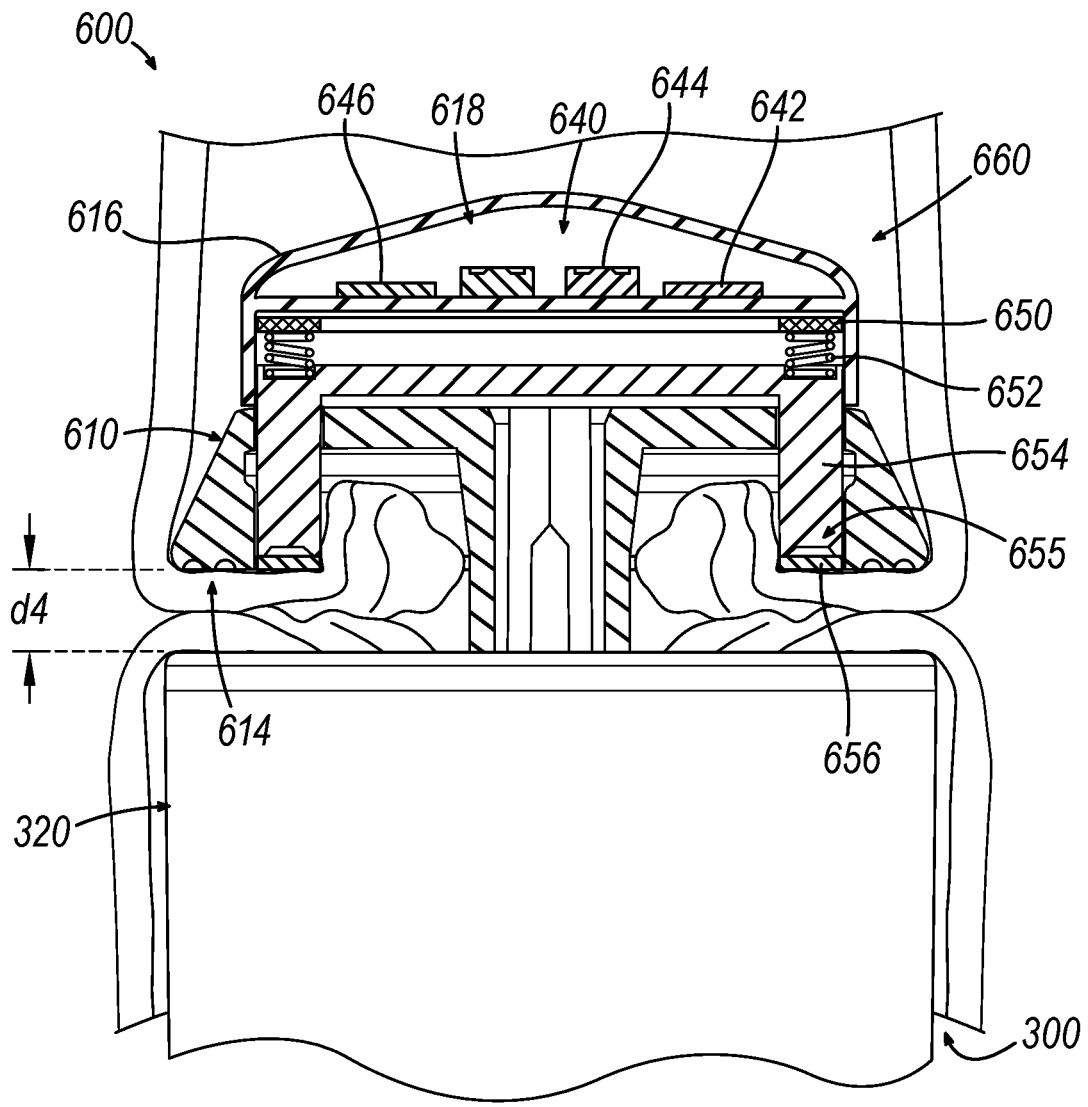
FIG. 13B depicts a cross-sectional side view of the anvil of FIG. 11 positioned within the first section of the digestive tract and the stapling head assembly of FIG. 4 positioned in the second section of the digestive tract, with the anvil retracted toward the stapling head assembly to thereby clamp tissue between the anvil and the stapling head assembly.

FIGS. 13A-13E show an illustrative use of anvil (600) with staple heard assembly (300) in order to perform an anastomosis. FIG. 13A shows trocar (330) inserted within central bore (622) such that pivoting latch members (630) suitably engage trocar (330), thereby coupling trocar (330) with anvil (600). With trocar (330) and anvil (600) coupled, a user may actuate anvil (600) proximally toward deck member (320) such that proximal surface (612) and deck member (320) clamps tissue with an increasing clamping force, as shown in FIG. 13B. It should be understood that spring (652) compresses as the clamping forces increase due to breakaway washer (656) engaging tissue. Breakaway washer (656) may engage tissue and compress spring (656) until breakaway washer (656) is substantial planar with proximal surface (612). Sensor (650) detects the compression of spring (656) in accordance with the description herein, and control unit (642) determines the tissue compression force, load, and/or pressure profile which anvil (600) and deck member (320) impart on grasped tissue. The tissue compression force, load, and/or pressure profile may be communicated to a user via wireless transmitter (644) in accordance with the teachings herein, thereby allowing a user to make informed decisions based on the determine tissue compression force, load, and/or pressure profile. A tissue gap distance (d4) is formed as shown in FIG. 13B.

Figure 13C:
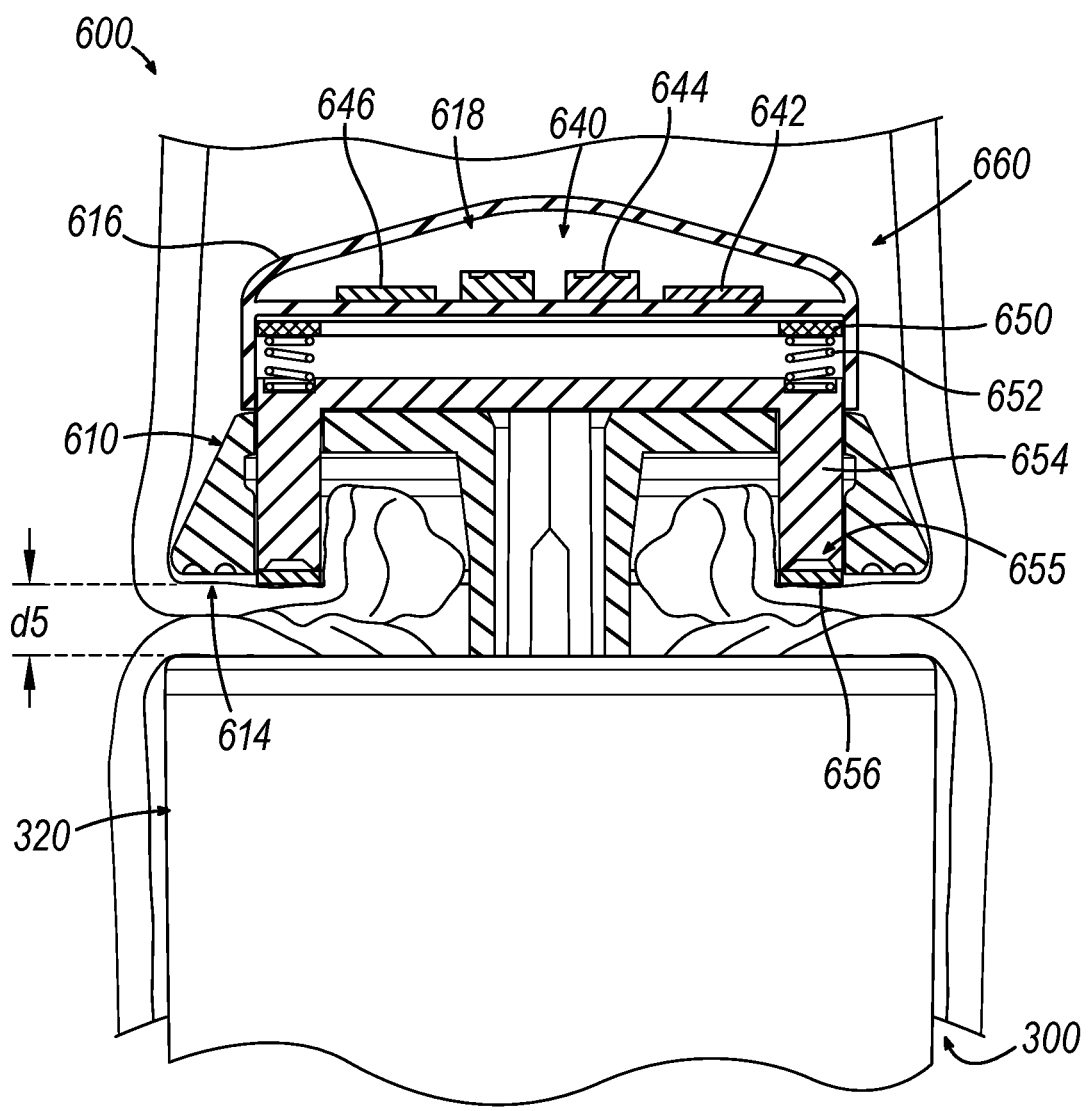
FIG. 13C depicts a cross-sectional side view of the anvil of FIG. 11 positioned within the first section of the digestive tract and the stapling head assembly of FIG. 4 positioned in the second section of the digestive tract, with the anvil retracted toward the stapling head assembly to thereby clamp tissue between the anvil and the stapling head assembly, with the pressure measuring assembly extending away from the head of the anvil thereby indicating a reduction in clamping pressure.
Figure 13D:
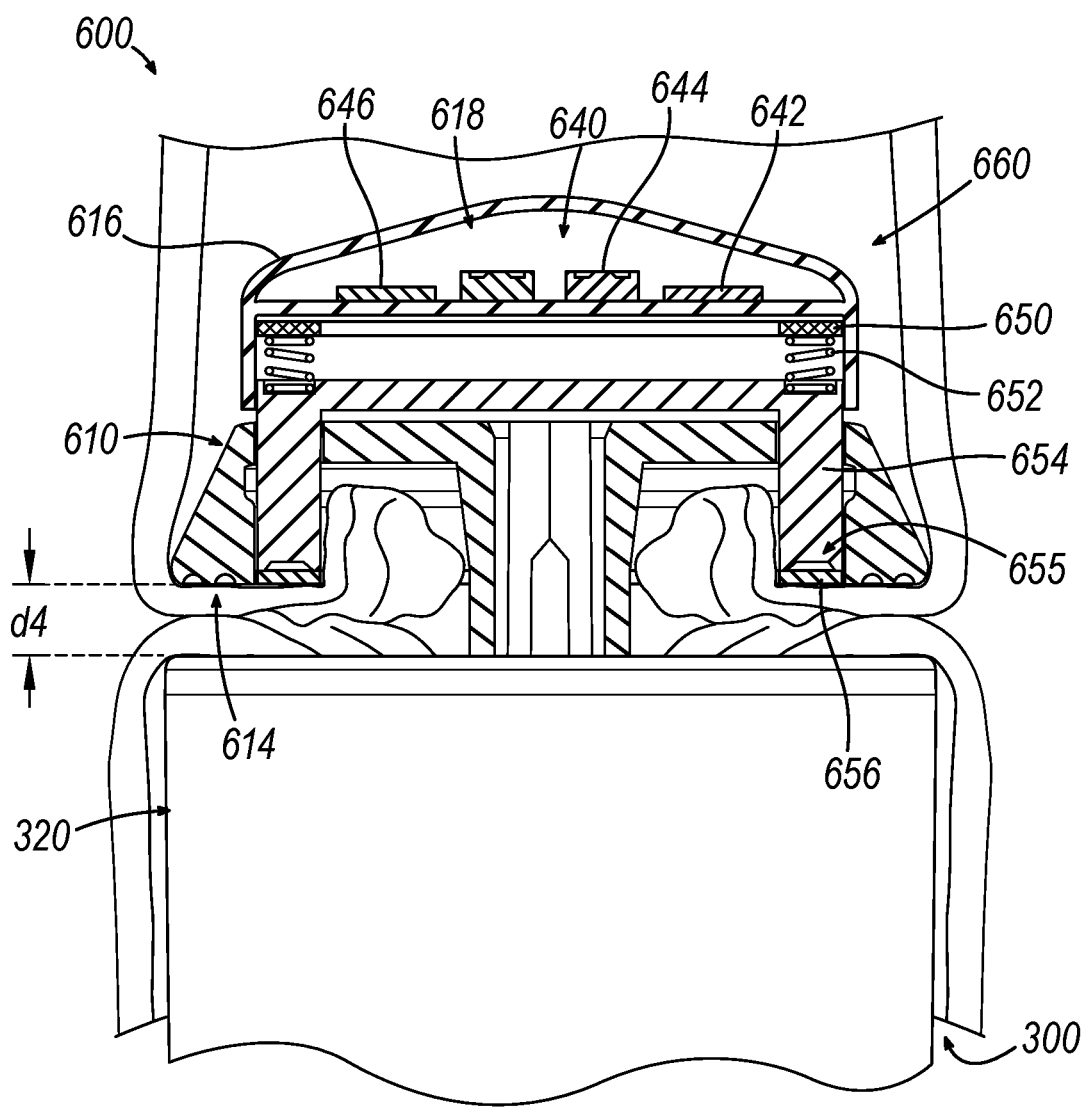
FIG. 13D depicts a cross-sectional side view of the anvil of FIG. 11 positioned within the first section of the digestive tract and the stapling head assembly of FIG. 4 positioned in the second section of the digestive tract, with the anvil further retracted toward the stapling head assembly to thereby further clamp tissue between the anvil and the stapling head assembly.

In some instances, as shown in FIGS. 13B-13C, the tissue compression forces may decrease due to a milking effect. In such instances, the tissue compression forces may decrease, thereby allowing spring (656) to elongate as shown in FIG. 13C, creating a smaller clamp distance (d5) between breakaway washer (656) and deck member (320). Sensor (650) detects the elongation of spring (656) in accordance with the description herein, and control unit (642) utilizes information from sensor (650) in order to determine the new tissue compression forces which anvil (600) and deck member (320) impart on grasped tissue. A user may make necessary adjustments prior to firing based on this information, such as further actuating anvil (600) toward deck member (320) until suitable tissue compression force, load, and/or pressure profile is achieved, such as the position shown in FIG. 13D.

Figure 13E:
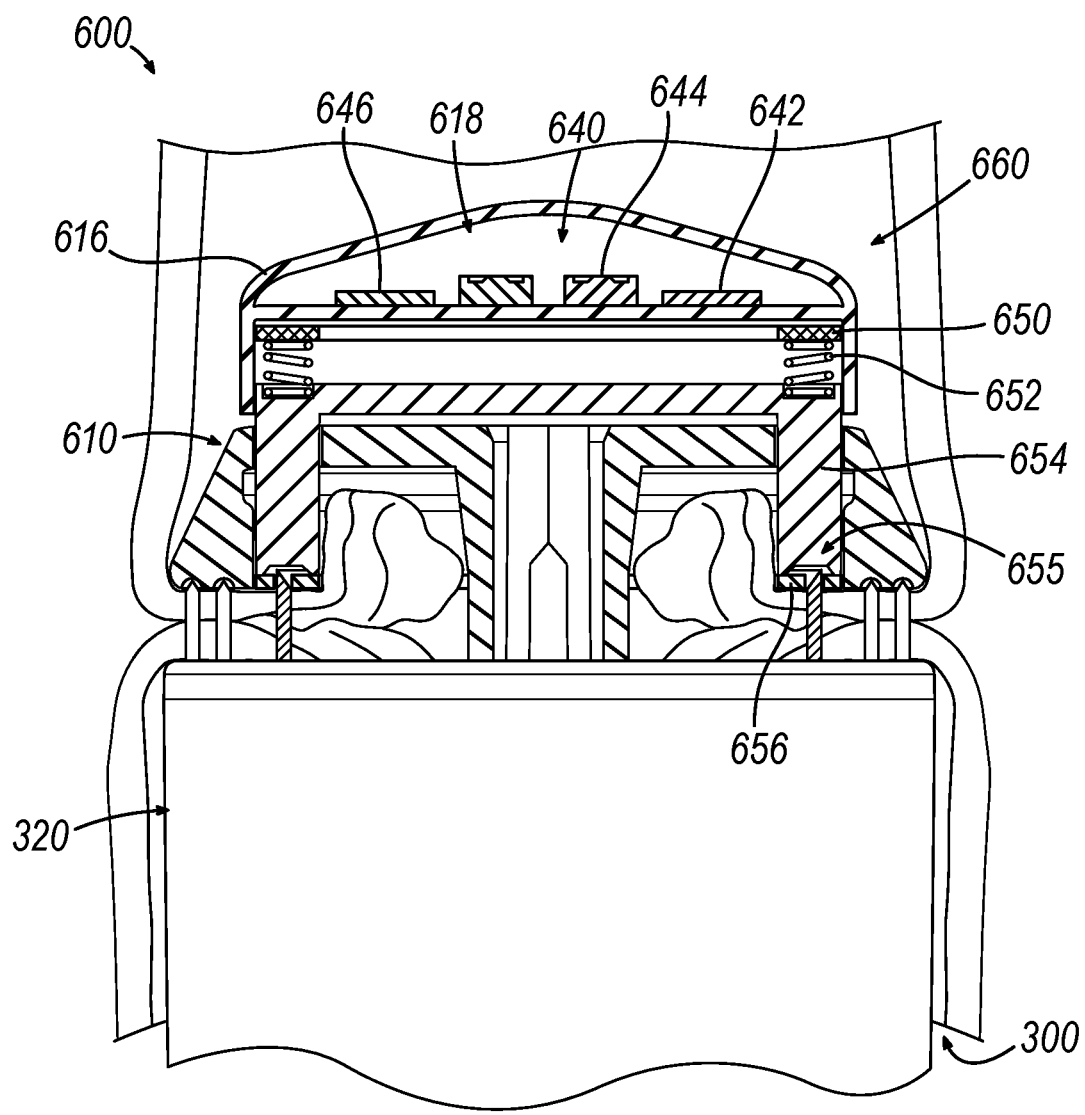
FIG. 13E depicts a cross-sectional side view of the anvil of FIG. 11 positioned within the first section of the digestive tract and the stapling head assembly of FIG. 4 positioned in the second section of the digestive tract, with the stapling head assembly actuated to sever and staple the clamped tissue.

Next, as shown in FIG. 13E, a user may fire staples and sever tissue in accordance with the description herein. Further, the user may remove both anvil (600) and staple head assembly (300), thereby leaving a completed anastomosis.

Figure 14:
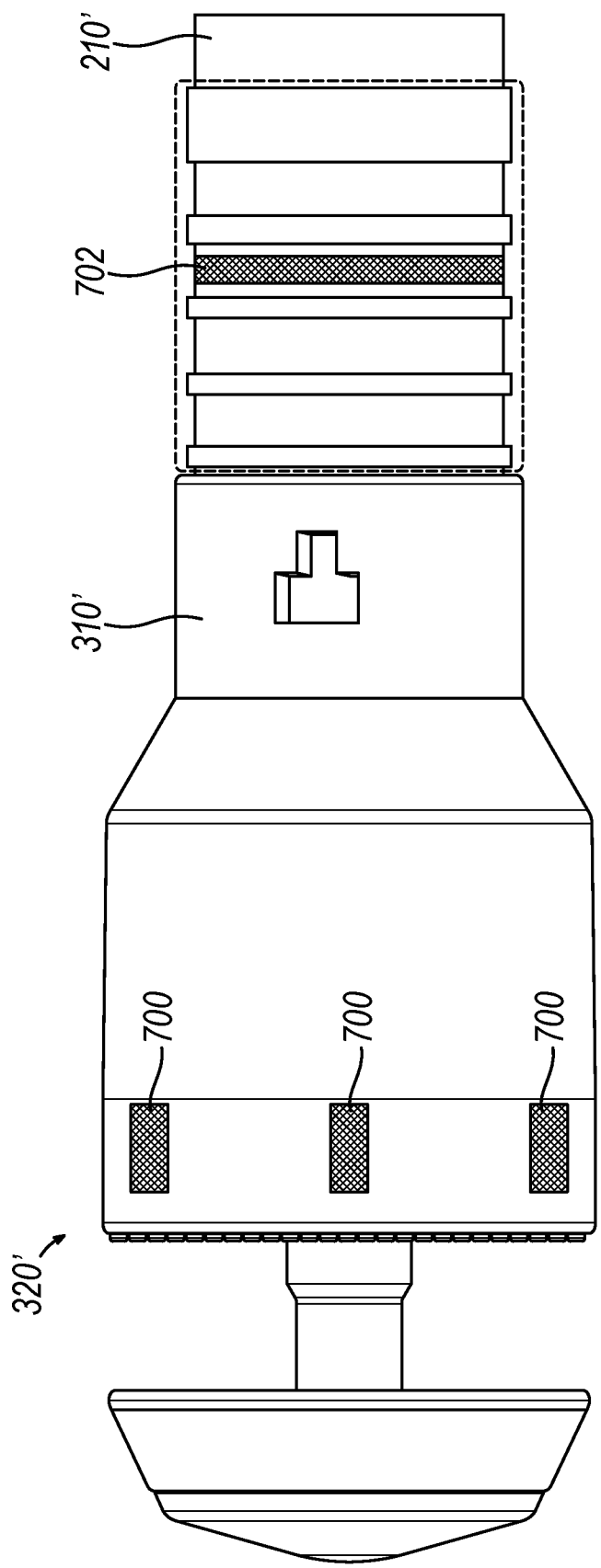
FIG. 14 depicts an elevational side view of an alternative stapling head assembly.

FIG. 14 shows an alternative outer sheath (210'), body member (310'), and deck member (320') that may be used in replacement is outer sheath (210), body member (310), and deck member (320) described above. Forces sensors (700) are interposed between deck member (320') and body member (310') and are configured to detect compression forces generated by anvil (400, 500, 600) compression tissue against deck member (320'). Deck member (320') compresses against body member (310') in response to tissue being compressed against deck member (320'). Therefore sensors (700) detect such compression and communicate the measured compression to a suitable controller (such as a surgeon's console having computing power and a display screen). Sensor (702) operates similar, but measure the compression of body member (310') against outer sheath (210') in response to tissue being compressed against deck member (320').

Figure 15:
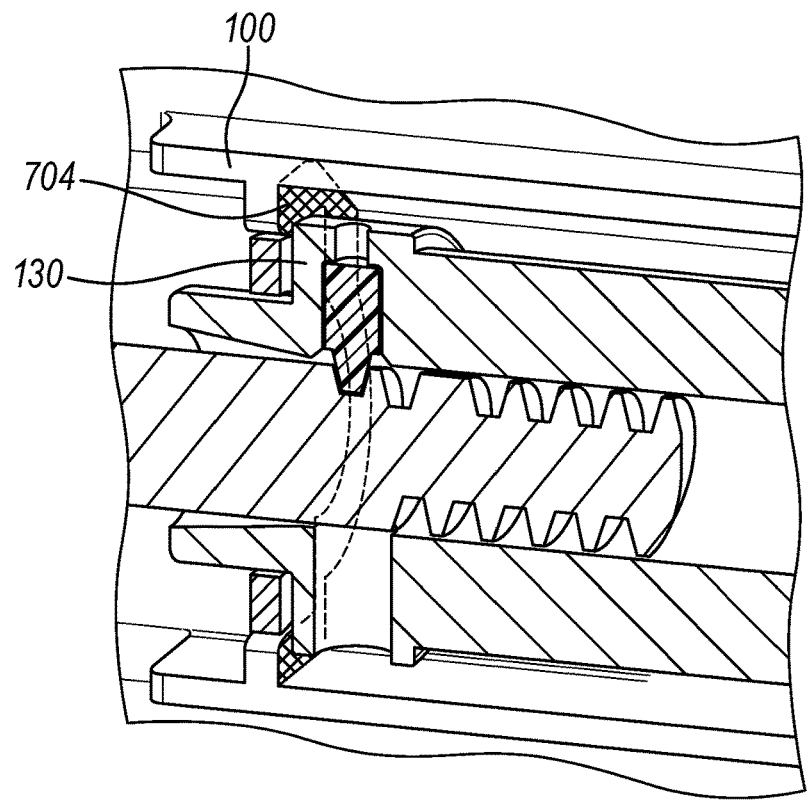
FIG. 15 depicts a perspective view of a load cell positioned within an alternative handle assembly.
Figure 16:
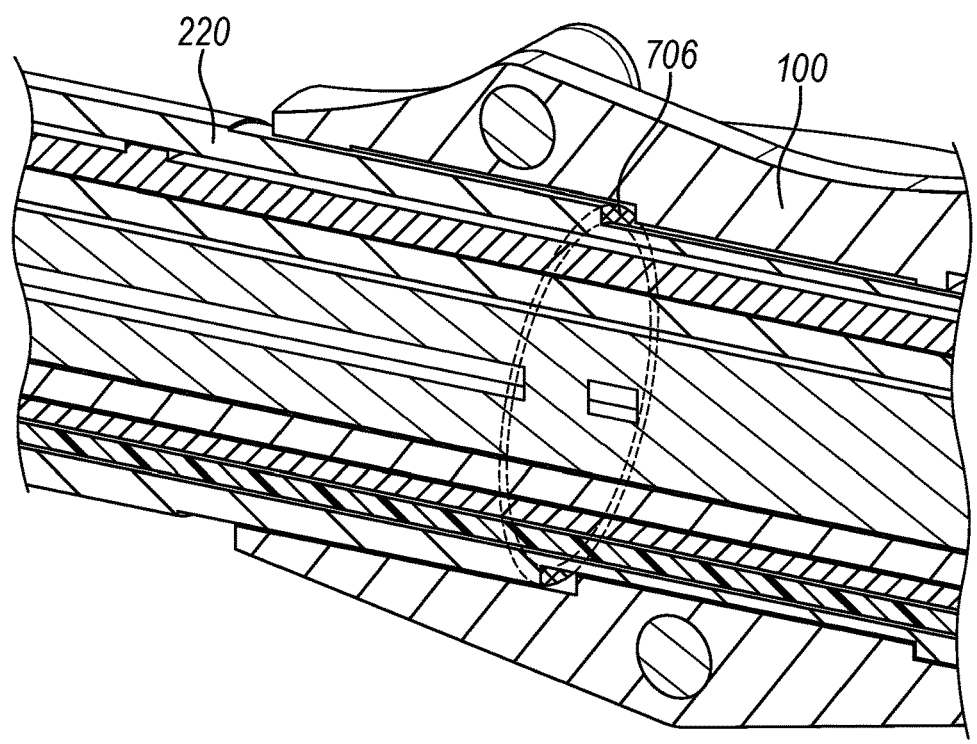
FIG. 16 depicts a perspective view of another load cell positioned within another alternative handle assembly.

FIGS. 15-16 show other placed load cells (704, 708) may be placed respectively, where load cells (704, 708) measures compression forces generated between other mechanical components of handle assembly (100) in response to grasping tissue in accordance with the description herein. FIG. 15 shows load cell (704) placed between a portion of handle assembly (100) and rotatable knob (130); while FIG. 16 shoes load cell (706) positioned between handle assembly (100) and outer sheath (210).

III. Examples of Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical stapler comprising: (a) a body assembly; (b) a shaft assembly that extends distally from the body assembly; (c) a stapling head assembly disposed at a distal end of the shaft assembly, wherein the stapling head assembly is operable to drive a plurality of staples into tissue, wherein the stapling head assembly comprises a closure shaft and a deck member, wherein the closure shaft is selectively movable longitudinally relative to the deck member; and (d) an anvil comprising: (i) a head comprising a proximally presented surface defining a plurality of staple forming pockets configured to form staples, wherein the proximally presented surface and the deck member of the stapling head assembly are configured to cooperatively grasp tissue; (ii) a shank extending proximally from the head, the shank configured to selectively couple with the closure shaft, (iii) a biasing body having a known spring constant, wherein the biasing body is interposed between the shank and the head such that the shank and the head are configured to move relative to each other, and (iv) an electronic unit comprising a distance sensor configured to measure a relative distance between the shank and the head, wherein the electronic unit is configured to communicate a parameter associated with the relative distance to a console.

Example 2

The surgical stapler of Example 1, wherein the electronic unit is fixed relative to the shank.

Example 3

The surgical stapler of either Example 1 or 2, wherein the distance sensor comprises a Hall Effect sensor, wherein a distally presented surface of the head comprises a magnet configured to interact with the Hall Effect sensor in order to measure the relative distance between the shank and the head.

Example 4

The surgical stapler of either Example 1 or 2, wherein the distance sensor comprises a light sensor, wherein a distally presented surface of the head comprise a reflective surface configured to interact with the light sensor in order to measure the relative distance between the shank and the head.

Example 5

The surgical stapler of any one or more of the preceding Examples, wherein the electronic unit further comprises a central camera located within a central bore defined by the shank.

Example 6

The surgical stapler of any one or more of the preceding Examples, wherein the electronic unit further comprises a first lateral camera facing toward a proximal direction.

Example 7

The surgical stapler of Example 6, wherein the first lateral camera comprises a light source.

Example 8

The surgical stapler of Example 7, wherein the electronic unit further comprises a second lateral camera facing toward the proximal direction.

Example 9

The surgical stapler of any one or more of the preceding Examples, wherein the biasing body comprises a spring, wherein the spring is fixed to the head at a first end, wherein the spring is fixed to the shank at a second end.

Example 10

The surgical stapler of any one or more of the preceding Examples, wherein the electronic unit comprises a control unit, wherein the control unit stores the known spring constant of the biasing body, wherein the control unit is configured to receive signals from the distance sensor indicative of the measured relative distance.

Example 11

The surgical stapler of Example 10, wherein the electronic unit further comprises a transmitter configured to transmit the signals received by the control unit.

Example 12

The surgical stapler of Example 11, wherein the electronic unit further comprises a battery configured to power the control unit and the transmitter.

Example 13

The surgical stapler of any one or more of the preceding Examples, wherein the proximally presented surface of the anvil comprises an annular shape.

Example 14

The surgical stapler of any one or more of the preceding Examples, wherein the shank comprises a pair of pivoting latch member configured to engage the closure shaft.

Example 15

The surgical stapler of any one or more of the preceding Examples, wherein the closure shaft comprises a trocar.

Example 16

A surgical stapler comprising: (a) a body assembly; (b) a shaft assembly that extends distally from the body assembly; (c) a stapling head assembly disposed at a distal end of the shaft assembly, wherein the stapling head assembly is operable to drive a plurality of staples into tissue, wherein the stapling head assembly comprises a closure shaft and a deck member, wherein the closure shaft is selectively movable longitudinally relative to the deck member; and (d) an anvil comprising: (i) a head comprising a proximally presented surface defining a plurality of staple forming pockets configured to form staples, wherein the proximally presented surface and the deck member of the stapling head assembly are configured to cooperatively grasp tissue, (ii) a shank extending proximally from the head, the shank configured to selectively couple with the closure shaft, (iii) a translating body configured to, in response to engaging tissue, translate between a proximal position relative to the proximally presented surface of the head and a flush position relative to the proximal presented surface of the head, (iv) a sensor configured to measure a force generated by the translating body being in engagement with tissue, and (v) an electronic unit configured to communicate a parameter associated with the measured force of the sensor to a console.

Example 17

The surgical instrument of Example 16, further comprising a spring interposed between the translating body and the sensor, wherein the spring biases the translating body into the proximal position.

Example 18

The surgical instrument of either Example 16 or 17, wherein the translating body further comprises a breakaway washer.

Example 19

The surgical instrument of claim either Example 16, 17, or 18, wherein the sensor comprises an annular shape.

Example 20

A surgical stapler comprising: (a) a body assembly; (b) a shaft assembly that extends distally from the body assembly; (c) a stapling head assembly disposed at a distal end of the shaft assembly, wherein the stapling head assembly is operable to drive a plurality of staples into tissue, wherein the stapling head assembly comprises a closure shaft and a deck member, wherein the closure shaft is selectively movable longitudinally relative to the deck member; and (d) an anvil comprising: (i) a head comprising a proximally presented surface defining a plurality of staple forming pockets configured to form staples, wherein the proximally presented surface and the deck member of the stapling head assembly are configured to cooperatively grasp tissue, (ii) a shank extending proximally from the head, the shank configured to selectively couple with the closure shaft, (iii) a camera associated with the head and facing in a proximal direction, and (iv) an electronic unit configured to wirelessly communicate images captured by the camera to a console.

IV. Miscellaneous

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as those made available by Auris Health, Inc. of Redwood City, CA or by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical stapler comprising:
   (a) a body;
   (b) a shaft that extends distally from the body;
   (c) a stapling head disposed at a distal end of the shaft, wherein the stapling head is operable to drive a plurality of staples into tissue, wherein the stapling head comprises a closure shaft and a deck, wherein the closure shaft is selectively movable longitudinally relative to the deck; and
   (d) an anvil comprising:
      (i) a head comprising a proximally presented surface defining a plurality of staple forming pockets configured to form staples, wherein the proximally presented surface and the deck of the stapling head are configured to cooperatively grasp tissue;
      (ii) a shank extending proximally from the head, the shank configured to selectively couple with the closure shaft,
      (iii) a biasing body having a known spring constant, wherein the biasing body is interposed between the shank and the head such that the shank and the head are configured to move relative to each other, and
      (iv) an electronic unit comprising a distance sensor configured to measure a relative distance between the shank and the head, wherein the electronic unit is configured to communicate a parameter associated with the relative distance to a console, wherein the electronic unit comprises a control unit, wherein the control unit stores the known spring constant of the biasing body, wherein the control unit is configured to receive signals from the distance sensor indicative of the measured relative distance.

2. The surgical stapler of claim 1, wherein the electronic unit is fixed relative to the shank.

3. The surgical stapler of claim 2, wherein the distance sensor comprises a Hall Effect sensor, wherein a distally presented surface of the head comprises a magnet configured to interact with the Hall Effect sensor in order to measure the relative distance between the shank and the head.

4. The surgical stapler of claim 2, wherein the distance sensor comprises a light sensor, and wherein a distally presented surface of the head comprise a reflective surface configured to interact with the light sensor in order to measure the relative distance between the shank and the head.

5. The surgical stapler of claim 1, wherein the electronic unit further comprises a central camera located within a central bore defined by the shank.

6. The surgical stapler of claim 1, wherein the electronic unit further comprises a first lateral camera facing toward a proximal direction.

7. The surgical stapler of claim 6, wherein the first lateral camera comprises a light source.

8. The surgical stapler of claim 7, wherein the electronic unit further comprises a second lateral camera facing toward the proximal direction.

9. The surgical stapler of claim 1, wherein the biasing body comprises a spring, wherein the spring is fixed to the head at a first end, wherein the spring is fixed to the shank at a second end.

10. The surgical stapler of claim 1, wherein the electronic unit further comprises a transmitter configured to transmit the signals received by the control unit.

11. The surgical stapler of claim 10, wherein the electronic unit further comprises a battery configured to power the control unit and the transmitter.

12. The surgical stapler of claim 1, wherein the proximally presented surface of the anvil comprises an annular shape.

13. The surgical stapler of claim 1, wherein the shank comprises a pair of pivoting latch member configured to engage the closure shaft.

14. The surgical stapler of claim 1, wherein the closure shaft comprises a trocar.

15. A surgical stapler comprising:
(a) a body;
(b) a shaft that extends distally from the body;
(c) a stapling head disposed at a distal end of the shaft, wherein the stapling head is operable to drive a plurality of staples into tissue, wherein the stapling head comprises a closure shaft and a deck, wherein the closure shaft is selectively movable longitudinally relative to the deck;
(d) an anvil comprising:
(i) a head comprising a proximally presented surface defining a plurality of staple forming pockets configured to form staples, wherein the proximally presented surface and the deck of the stapling head are configured to cooperatively grasp tissue,
(ii) a shank extending proximally from the head, the shank configured to selectively couple with the closure shaft,
(iii) a translating body configured to, in response to engaging tissue, translate between a proximal position relative to the proximally presented surface of the head and a flush position relative to the proximal presented surface of the head,
(iv) a sensor configured to measure a force generated by the translating body being in engagement with tissue, and
(v) an electronic unit configured to communicate a parameter associated with the measured force of the sensor to a console; and
(e) a spring interposed between the translating body and the sensor, wherein the spring biases the translating body into the proximal position.

16. The surgical instrument of claim 15, wherein the translating body further comprises a breakaway washer.

17. The surgical instrument of claim 15, wherein the sensor comprises an annular shape.

18. A surgical stapler comprising:
(a) a body;
(b) a shaft that extends distally from the body;
(c) a stapling head disposed at a distal end of the shaft, wherein the stapling head is operable to drive a plurality of staples into tissue, wherein the stapling head comprises a closure shaft and a deck, wherein the closure shaft is selectively movable longitudinally relative to the deck; and
(d) an anvil comprising:
(i) a head comprising a proximally presented surface defining a plurality of staple forming pockets configured to form staples, wherein the proximally presented surface and the deck of the stapling head are configured to cooperatively grasp tissue,
(ii) a shank extending proximally from the head, the shank configured to selectively couple with the closure shaft,
(iii) a camera associated with the head and facing in a proximal direction, and
(iv) an electronic unit configured to wirelessly communicate images captured by the camera to a console.

* * * * *